United States Patent
Brocke et al.

(10) Patent No.: US 12,297,386 B2
(45) Date of Patent: May 13, 2025

(54) AROMATIC ISOTHIOCYANATES

(71) Applicant: MERCK PATENT GMBH, Darmstadt (DE)

(72) Inventors: Constanze Brocke, Darmstadt (DE); Carsten Fritzsch, Darmstadt (DE); Dagmar Klass, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 90 days.

(21) Appl. No.: 18/032,993

(22) PCT Filed: Oct. 25, 2021

(86) PCT No.: PCT/EP2021/079439
§ 371 (c)(1),
(2) Date: Apr. 20, 2023

(87) PCT Pub. No.: WO2022/090098
PCT Pub. Date: May 5, 2022

(65) Prior Publication Data
US 2024/0117249 A1  Apr. 11, 2024

(30) Foreign Application Priority Data
Oct. 28, 2020  (EP) .................................... 20204317

(51) Int. Cl.
| | |
|---|---|
| *G02F 1/1333* | (2006.01) |
| *C07C 331/28* | (2006.01) |
| *C07D 309/04* | (2006.01) |
| *C07D 319/06* | (2006.01) |
| *C09K 19/12* | (2006.01) |
| *C09K 19/18* | (2006.01) |
| *C09K 19/30* | (2006.01) |
| *C09K 19/34* | (2006.01) |

(52) U.S. Cl.
CPC ............ *C09K 19/18* (2013.01); *C07C 331/28* (2013.01); *C07D 309/04* (2013.01); *C07D 319/06* (2013.01); *C09K 19/12* (2013.01); *C09K 19/30* (2013.01); *C09K 19/3059* (2013.01); *C09K 19/3402* (2013.01); *C07C 2601/02* (2017.05); *C07C 2601/14* (2017.05); *C09K 2019/122* (2013.01); *C09K 2019/123* (2013.01); *C09K 2019/181* (2013.01); *C09K 2019/183* (2013.01); *C09K 2019/3063* (2013.01); *C09K 2019/3422* (2013.01)

(58) Field of Classification Search
CPC ........ C09K 19/12; C09K 19/18; C09K 19/30; C09K 19/3059; C09K 19/3402; C09K 2019/181; C09K 2019/183; C09K 2019/3422; G02F 1/1333; C07D 309/04; C07D 319/06; C07C 2601/02
See application file for complete search history.

(56) References Cited

U.S. PATENT DOCUMENTS

| | | | |
|---|---|---|---|
| 7,361,288 B2 | 4/2008 | Lüssem et al. | |
| 10,711,197 B2 | 7/2020 | Wittek et al. | |
| 11,427,761 B2 | 8/2022 | Brocke et al. | |
| 11,891,557 B2 * | 2/2024 | Ushakov ................ | C09K 19/04 |
| 2021/0179943 A1 | 6/2021 | Horiguchi et al. | |
| 2024/0117249 A1 * | 4/2024 | Brocke .................. | C09K 19/18 |

FOREIGN PATENT DOCUMENTS

| | | |
|---|---|---|
| CN | 110746982 A | 2/2020 |
| EP | 3733816 A1 | 11/2020 |

OTHER PUBLICATIONS

International search report in corresponding PCT/EP2021/079439 dated Jan. 4, 2021 (pp. 1-3).

* cited by examiner

*Primary Examiner* — Geraldina Visconti
(74) *Attorney, Agent, or Firm* — MILLEN, WHITE, ZELANO & BRANIGAN, P.C.; Ryan R. Pool

(57) ABSTRACT

The present invention relates to a compound of formula G

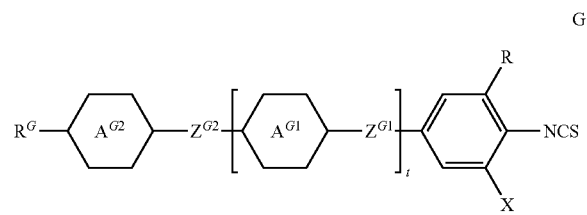

as defined in claim 1, to a liquid crystal medium comprising a compound of formula G and to high-frequency components comprising these media, especially microwave components for high-frequency devices, such as devices for shifting the phase of microwaves, tunable filters, tunable metamaterial structures, and electronic beam steering antennas, e.g. phased array antennas.

11 Claims, No Drawings

AROMATIC ISOTHIOCYANATES

The present invention relates to aromatic isothiocyanates, liquid-crystalline media comprising same, and to high-frequency components comprising these media, especially microwave components for high-frequency devices, such as devices for shifting the phase of microwaves, tunable filters, tunable metamaterial structures, and electronic beam steering antennas (e.g. phased array antennas), and to devices comprising said components.

Liquid-crystalline media have been used for many years in electro-optical displays (liquid crystal displays: LCDs) in order to display information. More recently, however, liquid-crystalline media have also been proposed for use in components for microwave technology, such as, for example, in DE 10 2004 029 429 A and in JP 2005-120208 (A).

A. Gaebler, F. Goelden, S. Müller, A. Penirschke and R. Jakoby "Direct Simulation of Material Permittivities using an Eigen-Susceptibility Formulation of the Vector Variational Approach", 12MTC 2009—International Instrumentation and Measurement Technology Conference, Singapore, 2009 (IEEE), pp. 463-467, describe the corresponding properties of the known liquid-crystal mixture E7 (Merck KGaA, Germany).

DE 10 2004 029 429 A describes the use of liquid-crystal media in microwave technology, inter alia in phase shifters. Therein, liquid-crystalline media with respect to their properties in the corresponding frequency range have been discussed and liquid-crystalline media based on mixtures of mostly aromatic nitriles and isothiocyanates have been shown.

In EP 2 982 730 A1, mixtures are described that completely consist of isothiocyanate compounds, wherein compounds are proposed and exemplified that contain up to two fluorine atoms next to the isothiocyanate group. Fluorine atoms are commonly used in mesogenic compounds to introduce polarity. Especially in combination with a terminal NCS group high dielectric anisotropy values can be achieved in particular when an NCS group in the 1-position has two fluorine atoms in its ortho positions as the overall molecular dipole is the sum of all individual dipoles of a molecule's partial structures.

On the other hand, a well balanced compromise with respect to the number of fluorine atoms has to be found as fluorine substitution often has a negative influence in the nematic phase properties of a compound. The negative effect can be more pronounced in the case of bulky substituents such as alkyl groups. Such compounds are hardly known from prior art related to display applications of liquid crystals as they usually exhibit high viscosity and low clearing temperatures.

The compositions available for the use in microwave applications are still afflicted with several disadvantages. It is required to improve these media with respect to their general physical properties, the shelf life and the stability under operation in a device. In view of the multitude of different parameters which have to be considered and improved for the development of liquid crystalline media for microwave application it is desirable to have a broader range of possible mixture components for the development of such liquid-crystalline media.

An object of the present invention is to provide a compound for the use in liquid crystalline media with improved properties relevant for the application in the microwave range of the electromagnetic spectrum.

This object is achieved in accordance with the invention by the compounds of the general formula G

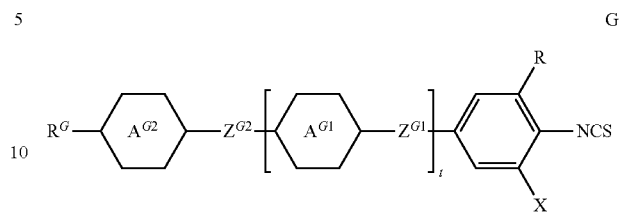

in which
$R^G$ denotes H, fluorinated or non-fluorinated, preferably non-fluorinated straight chain or branched alkyl having 1 to 12 C atoms, or fluorinated or non-fluorinated, preferably non-fluorinated straight chain or branched alkenyl having 2 to 12 C atoms in which one or more $CH_2$-groups may be replaced by

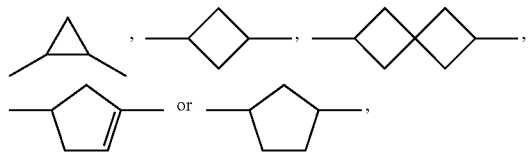

and in which one or more non-adjacent $CH_2$-groups may be replaced by —O—,
$Z^{G1}$, $Z^{G2}$ identically or differently, denote —CH=CH—, —CF=CF—, —CH=CF—, —CF=CH—, —C≡C—, —C≡C—C≡C— or a single bond, preferably —CF=CF—, —C≡C— or a single bond,
X denotes Cl or F, preferably F,
R denotes linear or branched or cyclic alkyl having 1 to 6 C atoms, preferably methyl, ethyl, isopropyl or cyclopropyl, very preferably methyl;
t is 0, 1 or 2, preferably 0 or 1, and

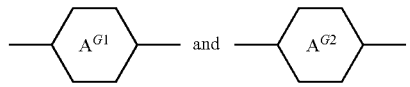

denote a radical selected from the following groups:
a) the group consisting of 1,4-phenylene, 1,4-naphthylene, and 2,6-naphthylene, in which one or two CH groups may be replaced by N and in which one or more H atoms may be replaced by L,
b) the group consisting of trans-1,4-cyclohexylene, 1,4-cyclohexenylene, tetralin-2,6-diyl, tetralin-5,8-diyl, decalin-2,6-diyl, bicyclo[1.1.1]pentane-1,3-diyl, 4,4'-bicyclohexylene, bicyclo[2.2.2]octane-1,4-diyl, and spiro[3.3]heptane-2,6-diyl, in which one or two CH groups may be replaced by N, one or more non-adjacent $CH_2$ groups may be replaced by —O— and/or —S— and in which one or more H atoms may be replaced by L,
c) the group consisting of thiophene-2,5-diyl, thieno[3,2-b]thiophene-2,5-diyl, selenophene-2,5-diyl, each of which may also be mono- or polysubstituted by L,
L on each occurrence, identically or differently, denotes F, Cl, CN, SCN, $SF_5$ or straight-chain or branched, in each case optionally fluorinated, alkyl, alkoxy, alkylcarbonyl, alkoxycarbonyl, alkylcarbonyloxy or alkoxycarbonyloxy each having 1 to 12 C atoms.

According to another aspect of the present invention there is provided a liquid crystal medium comprising one or more compounds of formula G.

Preferred embodiments of the present invention are subject-matter of the dependent claims or can also be taken from the description.

Surprisingly, it has been found that it is possible to achieve liquid-crystalline media having excellent stability and at the same time a high dielectric anisotropy, suitably fast switching times, a suitable, nematic phase range, high tunability and low dielectric loss in the microwave range of the electromagnetic spectrum by using compounds of formula G in liquid-crystalline media.

In particular, the compounds according to the invention enable media with a high tunability τ and show excellent miscibility with liquid crystal hosts especially those comprising similar polar compounds of the isothiocyanate type. As these polar compounds in general have limited solubility in a host material, it is possible to increase the overall proportion of compounds with high tunability in a medium and thus to achieve better tunabilities of media for microwave applications by addition of the compounds of formula G.

The media according to the present invention are distinguished by a high clearing temperature, a broad nematic phase range and excellent low-temperature stability (LTS). As a result, devices containing the media are operable under extreme temperature conditions.

The media are further distinguished by high values of the dielectric anisotropy and low rotational viscosities. As a result, the threshold voltage, i.e. the minimum voltage at which a device is switchable, is very low. A low operating voltage and low threshold voltage is desired in order to enable a device having improved switching characteristics and high energy efficiency. Low rotational viscosities enable fast switching of the devices according to the invention.

These properties as a whole make the media particularly suitable for use in components and devices for high-frequency technology and applications in the microwave range, in particular devices for shifting the phase of microwaves, tunable filters, tunable metamaterial structures, and electronic beam steering antennas (e.g. phased array antennas).

According to another aspect of the present invention there is thus provided a component and a device comprising said component, both operable in the microwave region of the electromagnetic spectrum. Preferred components are phase shifters, varactors, wireless and radio wave antenna arrays, matching circuits and adaptive filters.

Herein, "high-frequency technology" means applications of electromagnetic radiation having frequencies in the range of from 1 MHz to 1 THz, preferably from 1 GHz to 500 GHz, more preferably 2 GHz to 300 GHz, particularly preferably from about 5 GHz to 150 GHz.

As used herein, halogen is F, Cl, Br or I, preferably F or Cl, particularly preferably F.

Herein, alkyl is straight-chain or branched or cyclic and has 1 to 12 C atoms, is preferably straight-chain and has, unless indicated otherwise, 1, 2, 3, 4, 5, 6 or 7 C atoms and is accordingly preferably methyl, ethyl, n-propyl, n-butyl, n-pentyl, n-hexyl or n-heptyl.

Herein, branched alkyl is preferably isopropyl, s-butyl, isobutyl, 2-methylbutyl, isopentyl (3-methylbutyl), 2-methylhexyl or 2-ethylhexyl.

As used herein, cyclic alkyl is taken to mean straight-chain or branched alkyl or alkenyl having up to 12 C atoms, preferably alkyl having 1 to 7 C atoms, in which a group $CH_2$ is replaced with a carbocyclic ring having 3 to 5 C atoms, very preferably selected from the group consisting of cyclopropylalkyl, cyclobutylalkyl, cyclopentylalkyl and cyclopentenylalkyl.

Herein, an alkoxy radical is straight-chain or branched and contains 1 to 12 C atoms. It is preferably straight-chain and has, unless indicated otherwise, 1, 2, 3, 4, 5, 6 or 7 C atoms and is accordingly preferably methoxy, ethoxy, n-propoxy, n-butoxy, n-pentoxy, n-hexoxy or n-heptoxy.

Herein, an alkenyl radical is preferably an alkenyl radical having 2 to 12 C atoms, which is straight-chain or branched and contains at least one C—C double bond. It is preferably straight-chain and has 2 to 7 C atoms. Accordingly, it is preferably vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl. If the two C atoms of the C—C double bond are substituted, the alkenyl radical can be in the form of E and/or Z isomer (trans/cis). In general, the respective E isomers are preferred. Of the alkenyl radicals, prop-2-enyl, but-2- and -3-enyl, and pent-3- and -4-enyl are particularly preferred.

Herein, alkynyl is taken to mean an alkynyl radical having 2 to 12 C atoms, which is straight-chain or branched and contains at least one C—C triple bond. 1- and 2-propynyl and 1-, 2- and 3-butynyl are preferred.

Fluorinated alkyl-, alkoxy-, alkenyl or alkenyloxy can be branched or unbranched and is partially fluorinated, preferably perfluorinated. Preferably it is unbranched and has 1, 2, 3, 4, 5, 6 or 7 C atoms, in case of alkenyl 2, 3, 4, 5, 6 or 7 C atoms, very preferably it is selected from —$(CH_2)_n$—CH=$CF_2$, —$(CH_2)_n$—CH=CHF, —$(CH_2)_n$—CH=$Cl_2$, —$C_nF_{2n+1}$, —$(CF_2)_n$—$CF_2H$, —$(CH_2)_n$—$CF_3$, —$(CH_2)_n$—$CHF_2$, —$(CH_2)_n CH_2F$, —CH=$CF_2$, —$O(CH_2)_n$—CH=$CF_2$, —$OC_nF_{2n+1}$, —$O(CF_2)_n$—$CF_2H$, —$O(CH_2)_n CF_3$, —$O(CH_2)_n$—$CHF_2$, —$O(CF)_n CH_2F$, —OCF=$CF_2$, in which n is an integer from 0 to 7; in particular $OCF_3$.

The compounds of the general formula G are prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and are suitable for said reactions. Use can be made of variants which are known per se, but are not mentioned here in greater detail.

If desired, the starting materials can also be formed in situ by not isolating them from the reaction mixture, but instead by immediately reacting them further into the compounds of the general formula G.

The compounds of the formula G may be prepared in analogy to the processes described in EP 1 054 001 A1. A preferred synthetic pathway towards compounds according to the invention are exemplified in scheme 1 below in which the occurring groups and parameters have the meanings given for formula G. It is further illustrated by means of the working examples and can be adapted to the particular desired compounds of the general formula G by choice of suitable starting materials.

Preferred building blocks 2 (scheme 1) are for example 4-bromo-2-chloro-6-methyl-benzenamine, 4-bromo-2-fluoro-6-methyl-benzenamine, 4-bromo-2-chloro-6-ethyl-benzenamine or 4-bromo-2-ethyl-6-fluoro-benzenamine, all described in the literature, which can be reacted with suitable intermediates 1 to give compounds of the formula G, for example by cross coupling reactions commonly known as Sonogashira reactions (scheme 1, wherein $Z^{G1}$ is —C≡C— and G is H), Suzuki coupling (wherein $Z^{G1}$ is a single bond, —CH=CH—, —CF=CF—, —CH=CF— or —CF=CH— and G is a boronic acid or alkyl boronic ester group) and related transition metal catalyzed cross coupling reactions.

The compounds of formula N are reacted with a thiocarbonic acid derivative

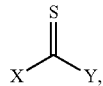

in which X and Y are leaving groups, or with CS$_2$ to give the compounds of formula G.

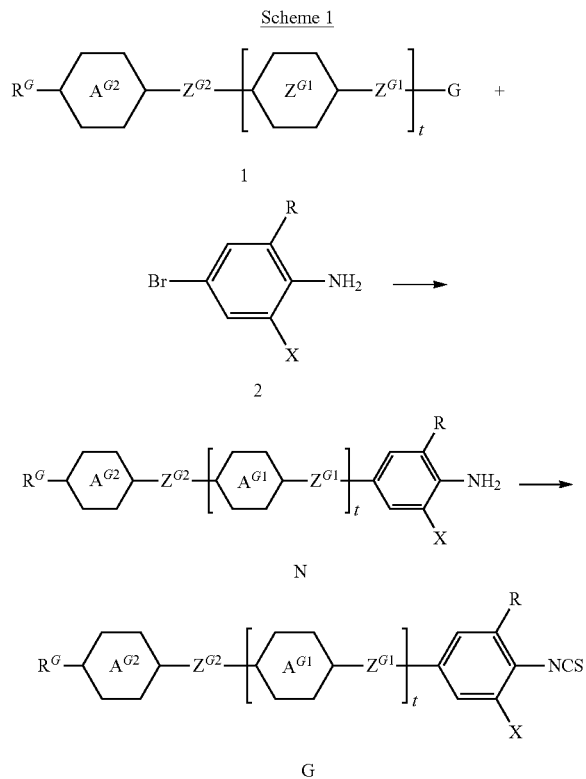

Preferred reagents for the process according to the invention for the transformation of compounds of the formula N into compounds of the formula G are carbon disulfide, thiophosgene, thiocarbonyl diimidazole, di-2-pyridyl thionocarbonate, bis(dimethylthiocarbamoyl) disulfide, dimethylthiocarbamoyl chloride and phenyl chlorothionoformate, very preferably thiophosgene.

The described reactions should only be regarded as illustrative. The person skilled in the art can carry out corresponding variations of the syntheses described and also follow other suitable synthetic routes in order to obtain compounds of the formula G.

The compounds of formula G are preferably selected from the group of compounds consisting of the formulae G-1 to G-6

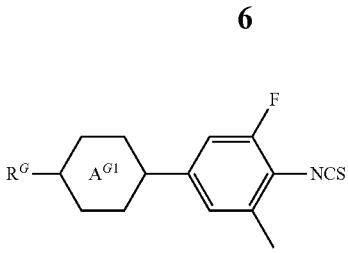

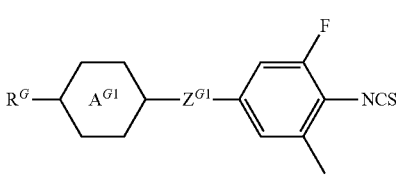

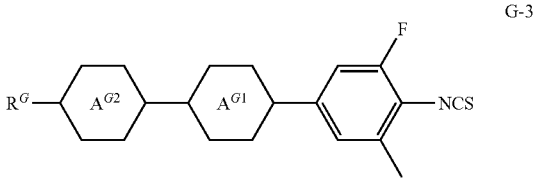

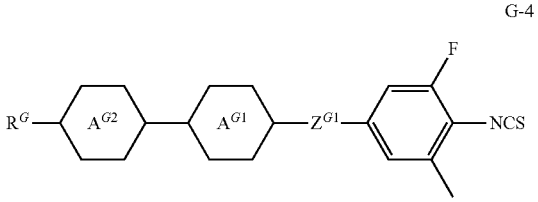

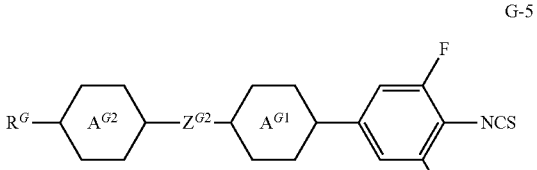

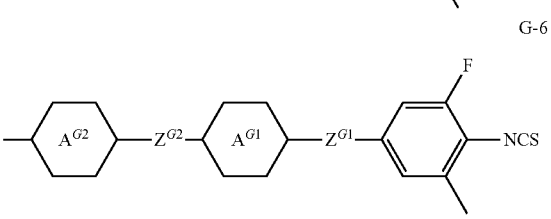

in which $R^G$, $Z^{G1}$, $Z^{G2}$,

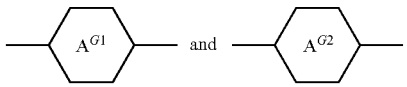

have the meanings given above for formula G, and preferably $Z^{G1}$, $Z^{G2}$ identically or differently, denote —CF=CF— or —C≡C—, $R^G$ denotes straight chain or branched or cyclic alkyl or alkenyl having 1 to 7 C atoms, and

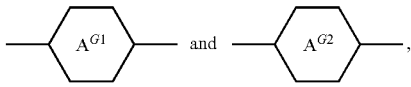

identically or differently, preferably denote
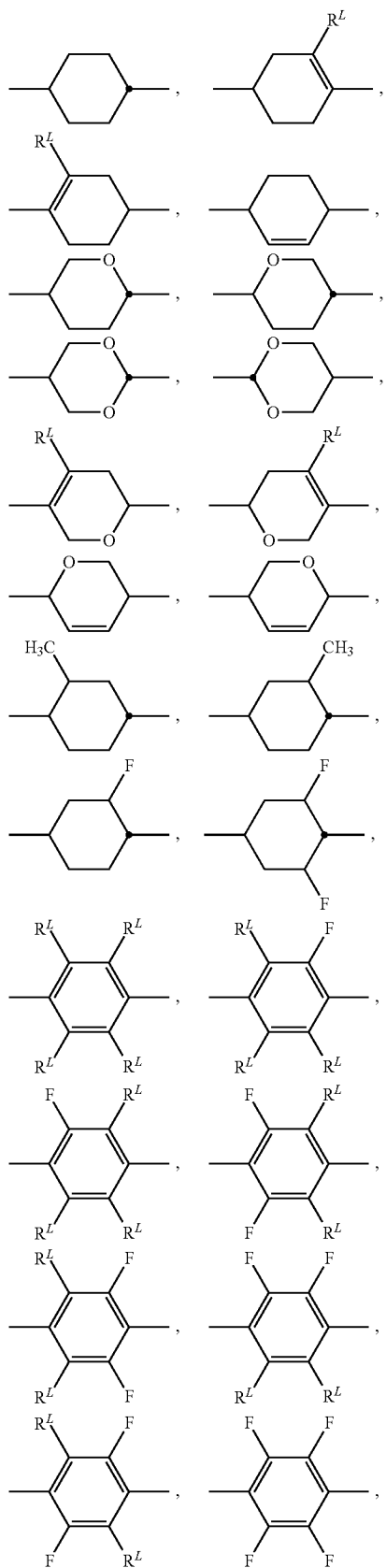
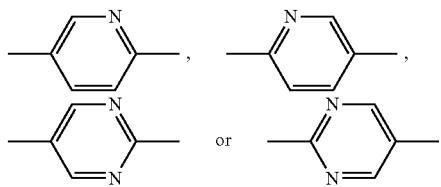
in which $R^L$, on each occurrence, identically or differently, denotes H or alkyl having 1 to 6 C atoms,
or denote
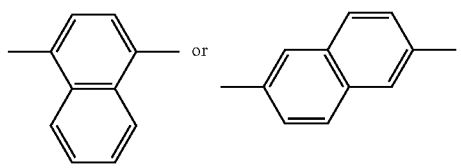
in which one or more H atoms may be replaced by a group $R^L$ or F, and in which
$R^L$ denotes H or alkyl having 1 to 6 C atoms; very preferably
denotes
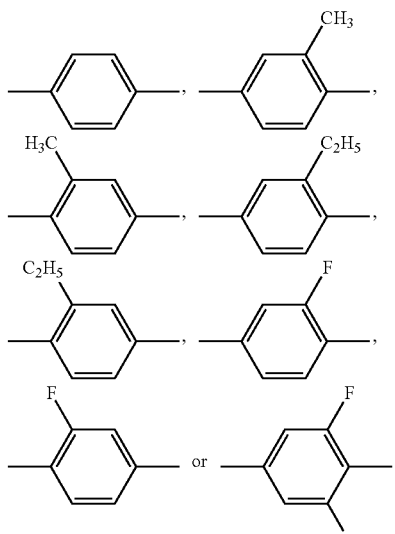
and

denotes
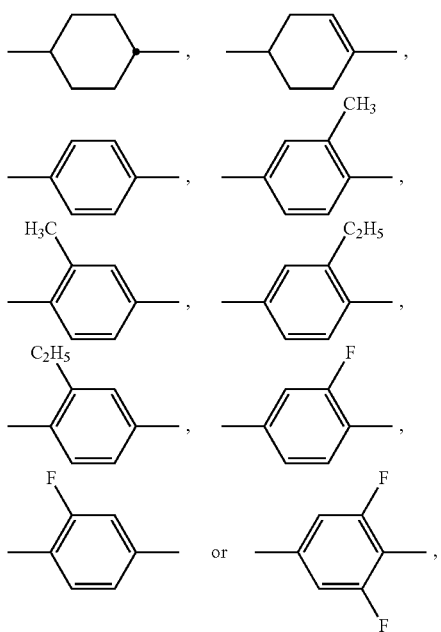
in particular
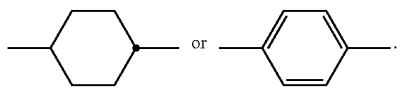
Very preferred compounds of formula G are selected from the following sub-formulae:
G-1-1
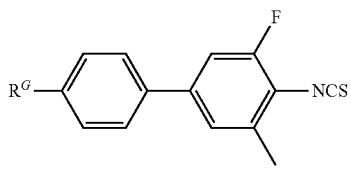
G-2-1
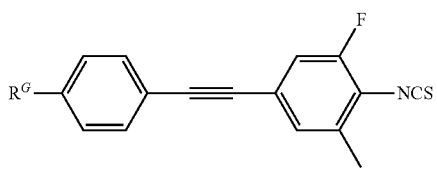
G-2-2
G-2-3
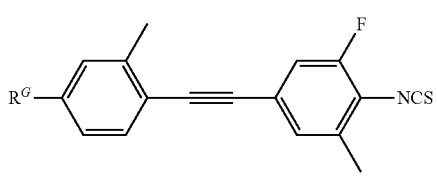
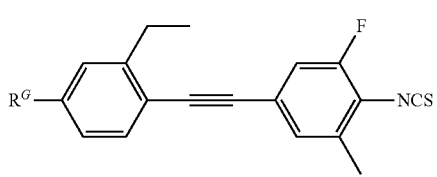
G-2-4
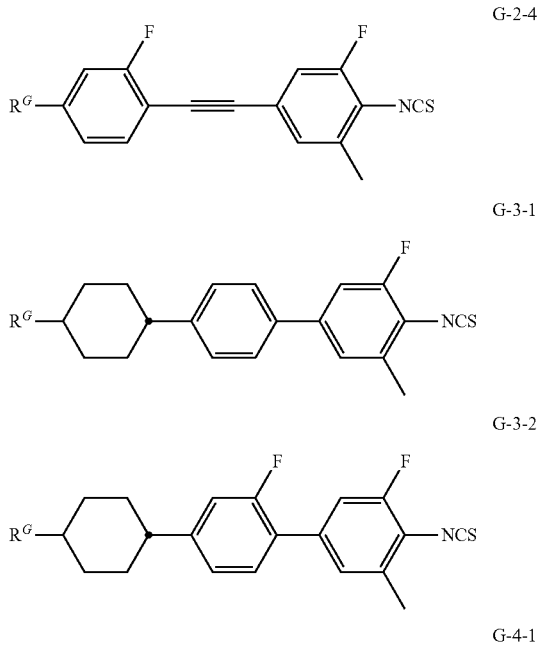
G-3-1
G-3-2
G-4-1
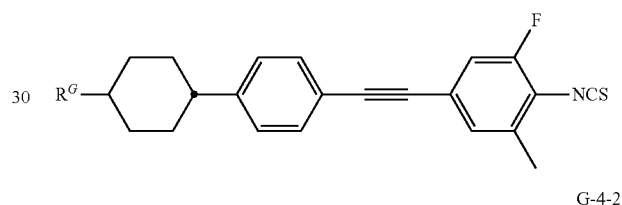
G-4-2
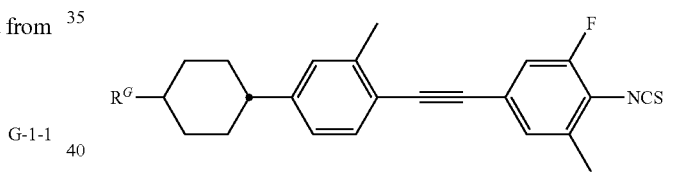
G-4-3
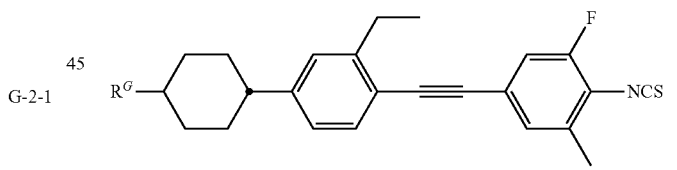
G-4-4
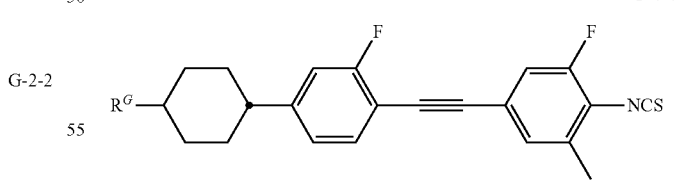
G-4-5
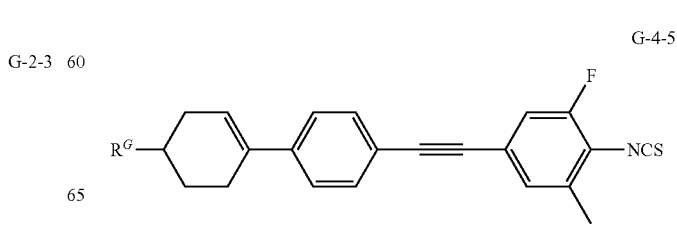

G-4-6
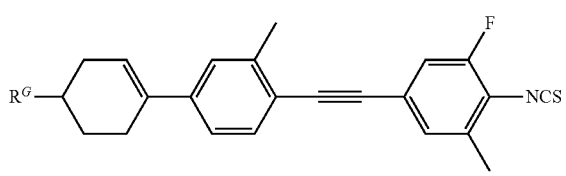

G-4-7
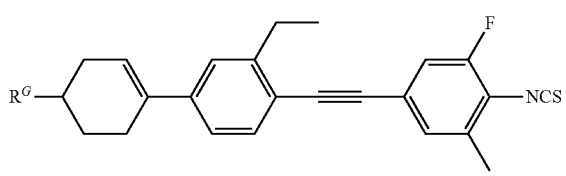

G-4-8
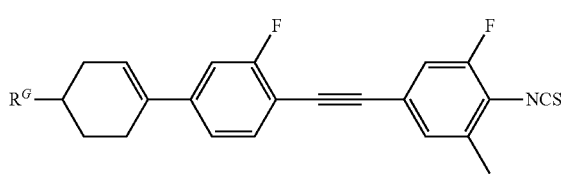

G-4-9
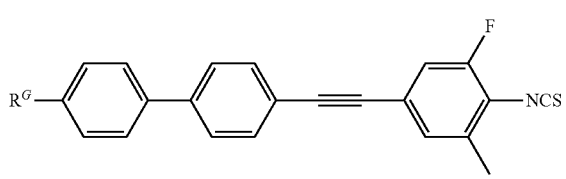

G-4-10
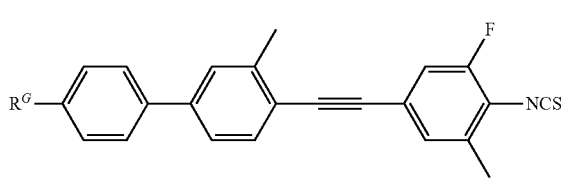

G-4-11
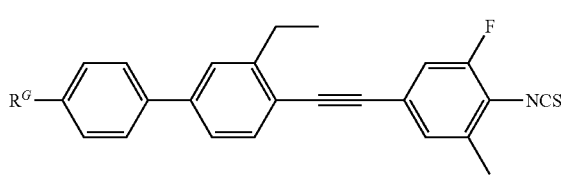

G-4-12
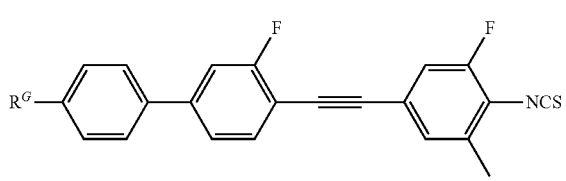

G-5-1
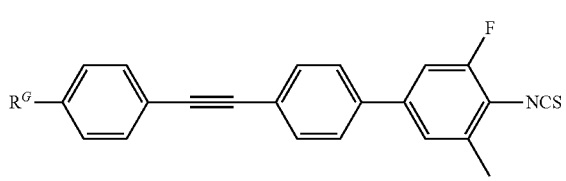

G-5-2
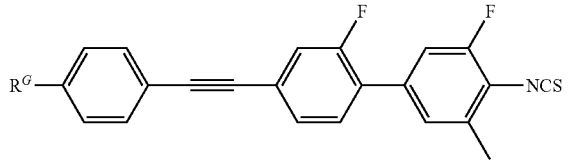

G-5-3
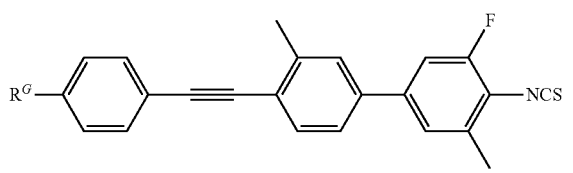

G-5-4
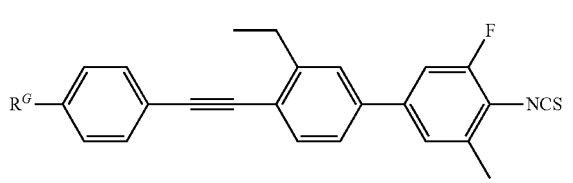

G-5-5
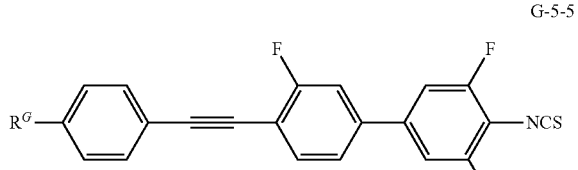

in which $R^G$ has the meanings given above and preferably denotes straight chain or branched alkyl having 1 to 7 C atoms, in particular methyl, ethyl, n-propyl, n-butyl, n-pentyl, n-hexyl or n-heptyl.

According to another aspect of the present invention there is provided a liquid crystal medium comprising one or more compounds of formula G. Preferably, the medium comprises one or more compounds selected from the group of the formulae I, II and III:

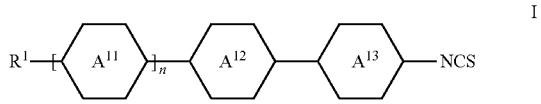
I

II

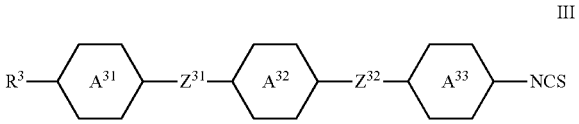
III in which $R^1$ denotes H, non-fluorinated alkyl or non-fluorinated alkoxy having 1 to 17, preferably 2 to 10 C atoms, or non-fluorinated alkenyl, non-fluorinated alkenyloxy or non-fluorinated alkoxyalkyl having 2 to 15, preferably 3 to 10, C atoms, in which one or more $CH_2$-groups may be replaced by

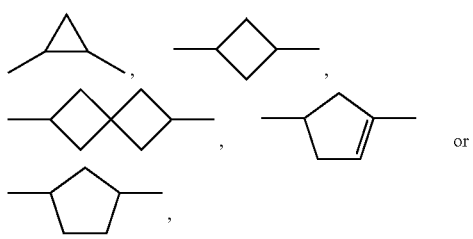

preferably non-fluorinated alkyl or non-fluorinated alkenyl, n is 0, 1 or 2,

to

on each occurrence, independently of one another, denote

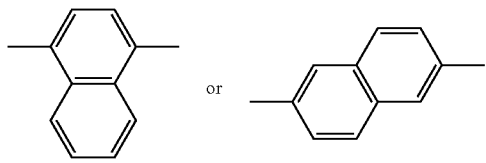

in which $R^L$, on each occurrence, identically or differently, denotes H or alkyl having 1 to 6 C atoms, preferably H, methyl or ethyl, particularly preferably H, or in which one or more H atoms may be replaced by a group $R^L$ or F, and wherein

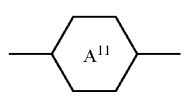

alternatively denotes

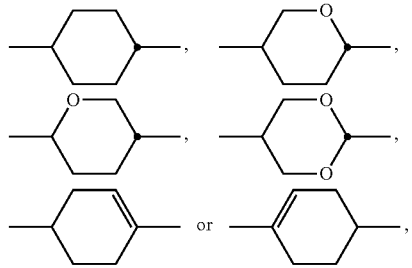

preferably

and in case n=2, one of

preferably denotes

and the other preferably denotes

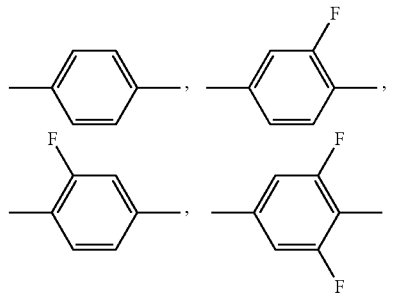

;

preferably

to

, independently of one another, denote

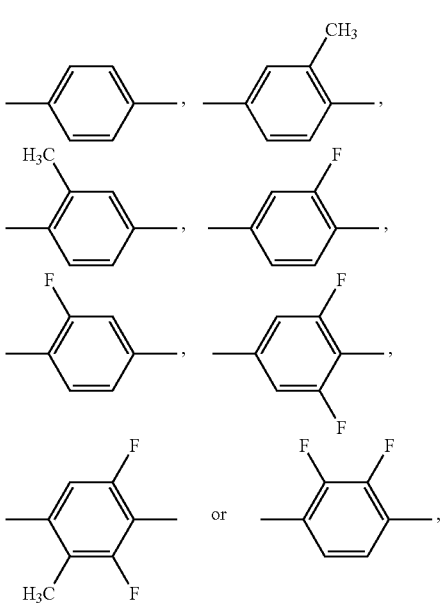

more preferably

denotes

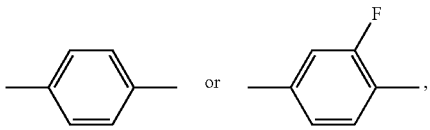, denotes

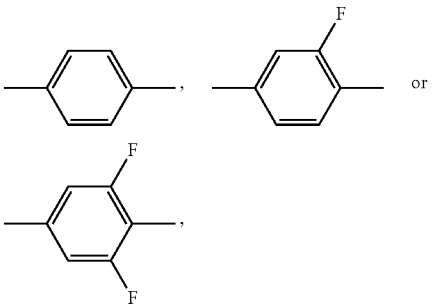

denotes

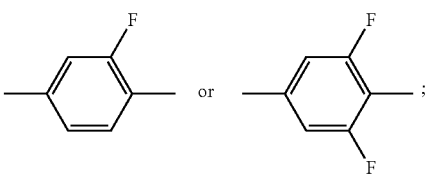;

R² denotes H, non-fluorinated alkyl or non-fluorinated alkoxy having 1 to 17, preferably 2 to 10 C atoms, or non-fluorinated alkenyl, non-fluorinated alkenyloxy or non-fluorinated alkoxyalkyl having 2 to 15, preferably 3 to 10, C atoms, in which one or more CH₂-groups may be replaced by

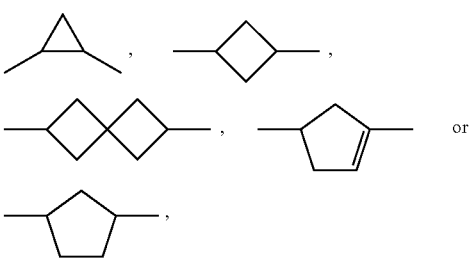

preferably non-fluorinated alkyl or non-fluorinated alkenyl,
Z²¹ denotes trans-CH═CH—, trans-CF═CF— or —C≡C—, preferably —C≡C— or trans-CH═CH—, and

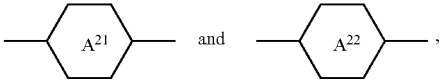

independently of one another, denote

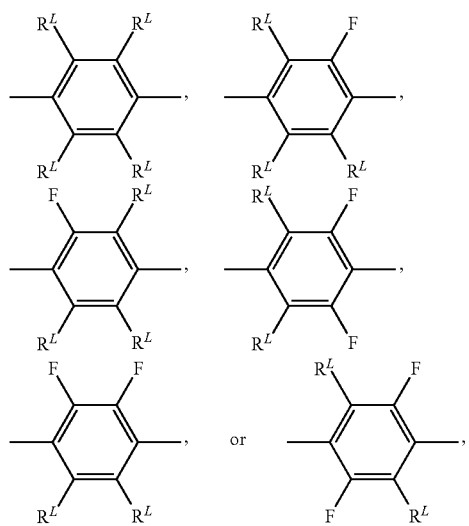

in which $R^L$, on each occurrence, identically or differently, denotes H or alkyl having 1 to 6 C atoms, preferably H, methyl or ethyl, particularly preferably H, or

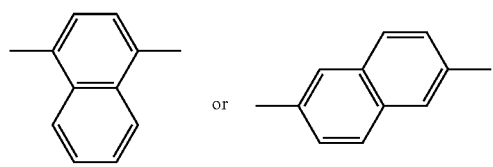

in which one or more H atoms may be replaced by a group $R^L$ or F, preferably

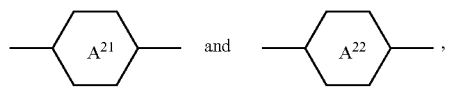

independently of one another, denote

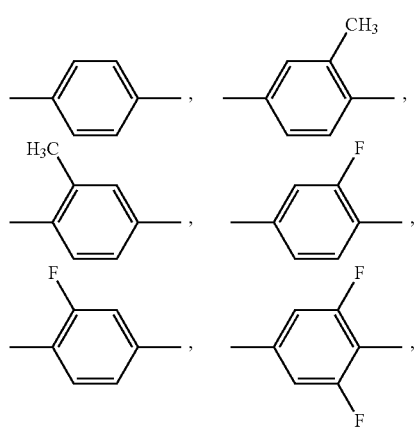

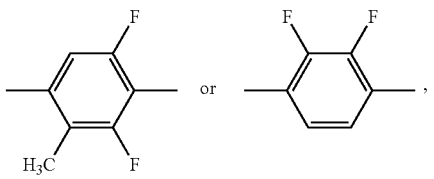

preferably denotes

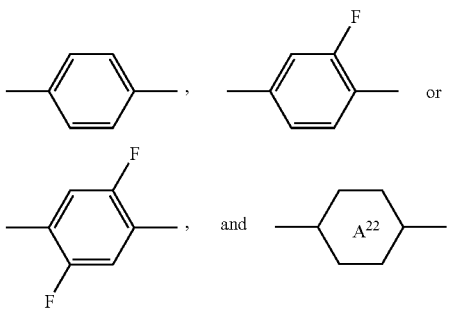

preferably denotes

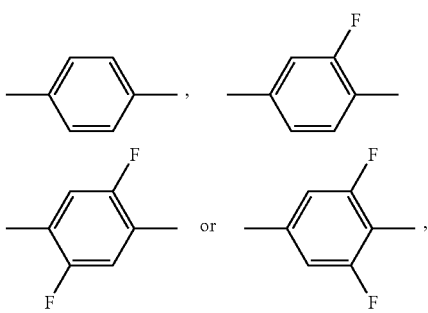

more preferably

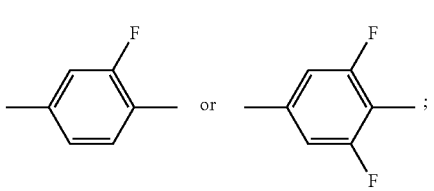

$R^3$ denotes H, non-fluorinated alkyl or non-fluorinated alkoxy having 1 to 17, preferably 2 to 10 C atoms, or non-fluorinated alkenyl, non-fluorinated alkenyloxy or non-fluorinated alkoxyalkyl having 2 to 15, preferably 3 to 10, C atoms, in which one or more $CH_2$-groups may be replaced by

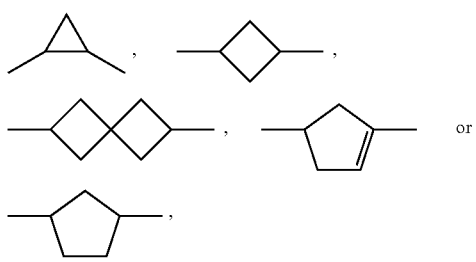

preferably non-fluorinated alkyl or non-fluorinated alkenyl,
one of $Z^{31}$ and $Z^{32}$, preferably $Z^{32}$; denotes trans-CH=CH—, trans-CF=CF— or —C≡C— and the other one, independently thereof, denotes —C≡C—, trans-CH=CH—, trans-CF=CF— or a single bond, preferably one of them, preferably $Z^{32}$ denotes —C≡C— or trans-CH=CH— and the other denotes a single bond, and

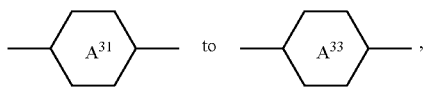

independently of one another, denote

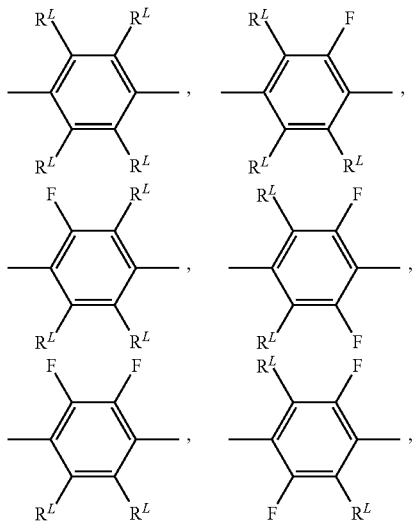

in which $R^L$, on each occurrence, identically or differently, denotes H or alkyl having 1 to 6 C atoms, preferably H, methyl or ethyl, particularly preferably H,
or

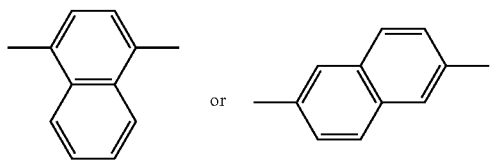

in which one or more H atoms may be replaced by a group $R^L$ or F,
and wherein

alternatively denotes or

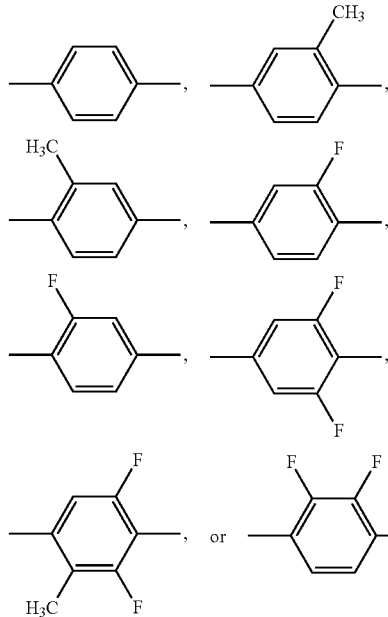

preferably

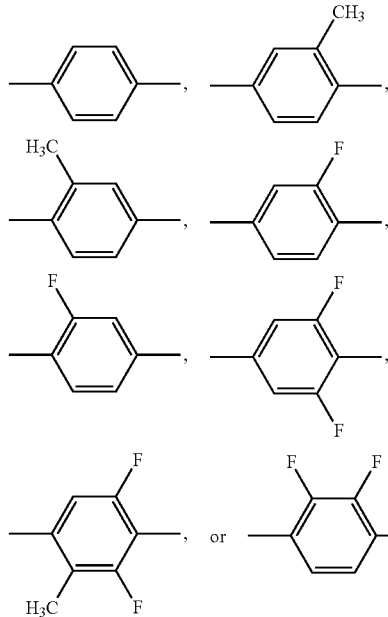

to independently of one another, denote denotes

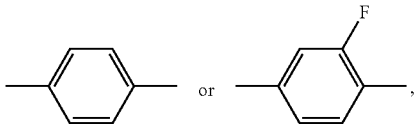

denotes

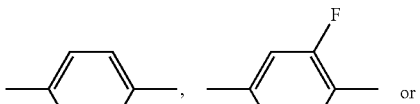

in particular

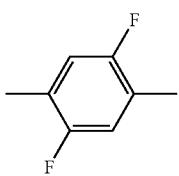

denotes

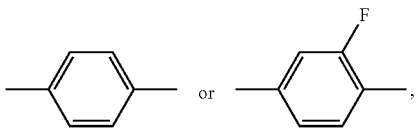

denotes

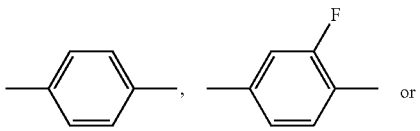

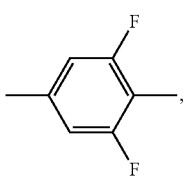

in particular

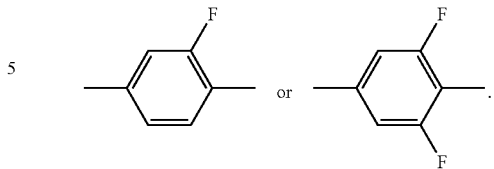

In the compounds of the formulae I, II and III, $R^L$ preferably denotes H.

In another preferred embodiment, in the compounds of formulae I, II and III, one or two groups $R^L$, preferably one group $R^L$ is different from H.

In a preferred embodiment of the present invention, the compounds of formula I are selected from the group of compounds of the formulae I-1 to I-5:

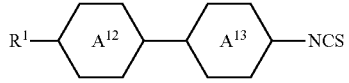

I-1

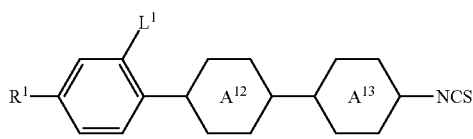

I-2

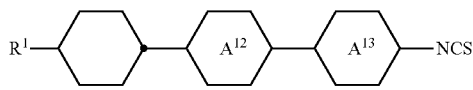

I-3

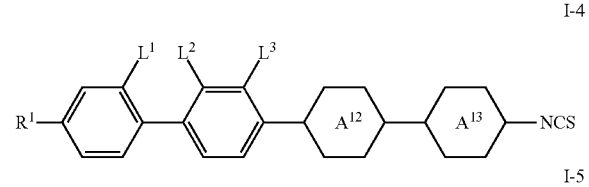

I-4

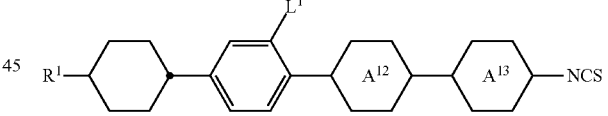

I-5 in which
$L^1$, $L^2$ and $L^3$ on each occurrence, identically or differently, denote H or F, and the other groups have the respective meanings indicated above for formula I and preferably
$R^1$ denotes non-fluorinated alkyl having 1 to 7 C atoms or non-fluorinated alkenyl having 2 to 7 C atoms.

The media preferably comprise one or more compounds of formula I-1, which are preferably selected from the group of the compounds of the formulae I-1a to I-1d, preferably of formula I-1b:

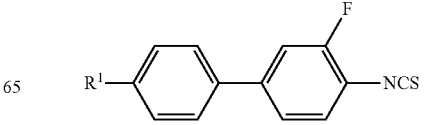

I-1a

-continued

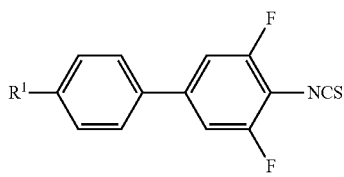
I-1b

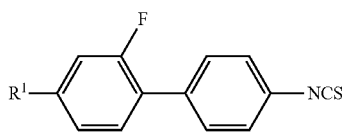
I-1c

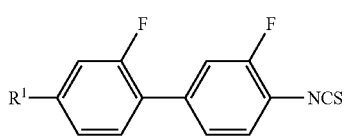
I-1d in which R¹ has the meaning indicated above for formula I and preferably denotes non-fluorinated alkyl having 1 to 7 C atoms or non-fluorinated alkenyl having 2 to 7 C atoms.

The media preferably comprise one or more compounds of formula I-2, which are preferably selected from the group of the compounds of the formulae I-2a to I-2e, preferably of formula I-2c:

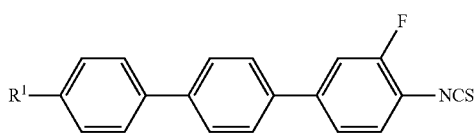
I-2a

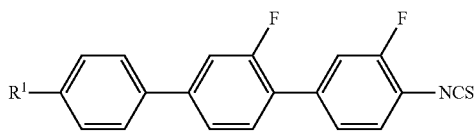
I-2b

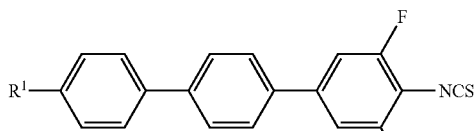
I-2c

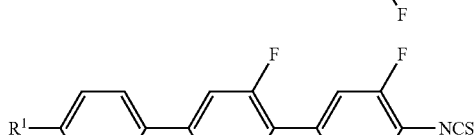
I-2d

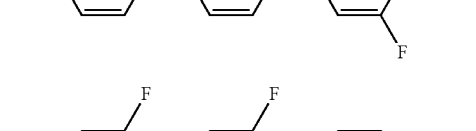
I-2e in which R¹ has the meaning indicated above for formula I and preferably denotes non-fluorinated alkyl having 1 to 7 C atoms or non-fluorinated alkenyl having 2 to 7 C atoms.

The media preferably comprise one or more compounds of formula I-3, which are preferably selected from the group of the compounds of the formulae I-3a to I-3d, particularly preferably of formula I-3b:

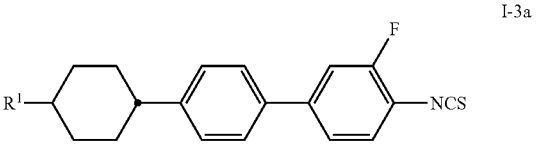
I-3a

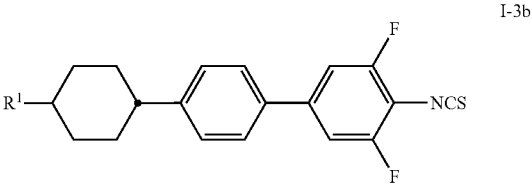
I-3b

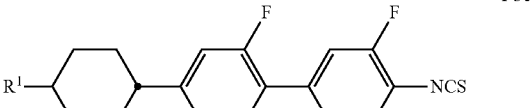
I-3c

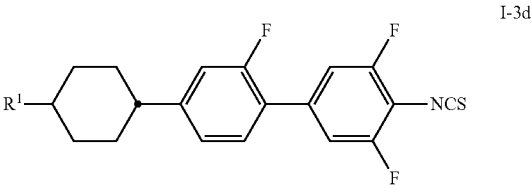
I-3d in which R¹ has the meaning indicated above for formula I and preferably denotes non-fluorinated alkyl having 1 to 7 C atoms or non-fluorinated alkenyl having 2 to 7 C atoms.

The media preferably comprise one or more compounds of formula I-4, which are preferably selected from the group of the compounds of the formulae I-4a to I-4e, particularly preferably of formula I-4b:

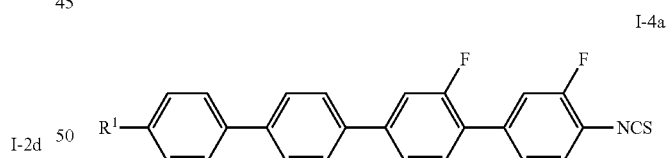
I-4a

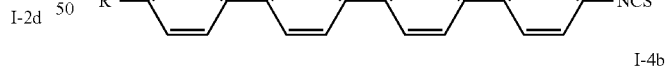
I-4b

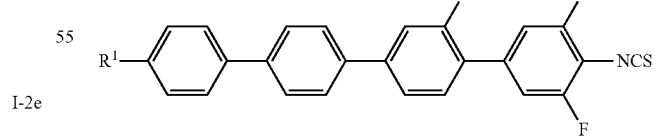

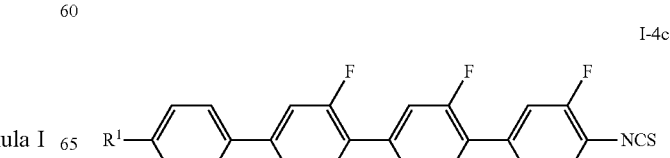
I-4c

I-4d

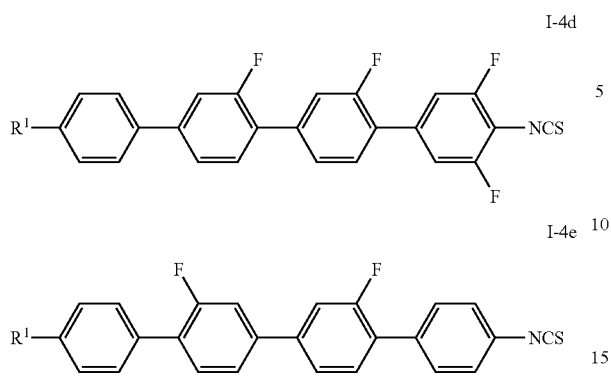

I-4e in which R¹ has the meaning indicated above for formula I and preferably denotes non-fluorinated alkyl having 1 to 7 C atoms or non-fluorinated alkenyl having 2 to 7 C atoms.

The media preferably comprise one or more compounds of formula I-5, which are preferably selected from the group of the compounds of the formulae I-5a to I-5d, particularly preferably of formula I-5b:

I-5a

I-5b

I-5c

I-5d in which R¹ has the meaning indicated above for formula I and preferably denotes non-fluorinated alkyl having 1 to 7 C atoms or non-fluorinated alkenyl having 2 to 7 C atoms.

The media preferably comprise one or more compounds of formula II, which are preferably selected from the group of the compounds of the formulae II-1 to II-3, preferably selected from the group of the compounds of the formulae II-1 and II-2:

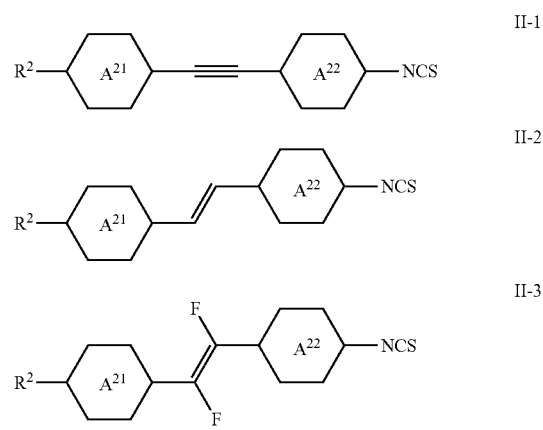

II-1

II-2

II-3 in which the occurring groups have the meanings given under formula II above and preferably R² denotes non-fluorinated alkyl or alkoxy having 1 to 7 C atoms or non-fluorinated alkenyl having 2 to 7 C atoms, and one of

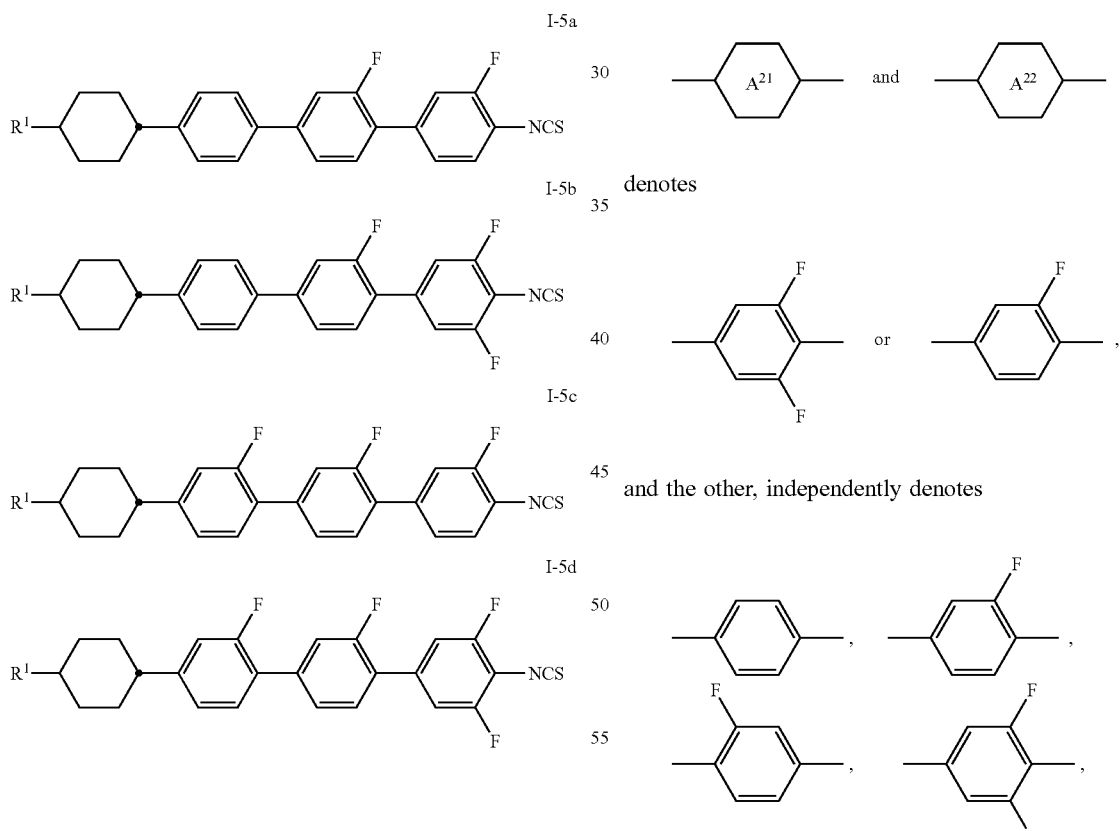

denotes or and the other, independently denotes or preferably

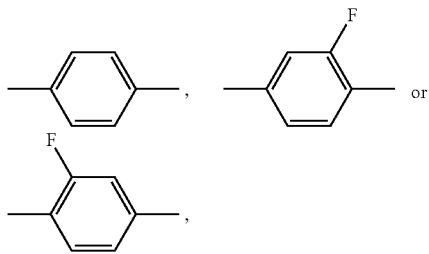

most preferably

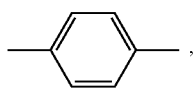

and preferably

R² denotes $C_nH_{2n+1}$ or $CH_2=CH-(CH_2)_z$, and
n denotes an integer in the range from 1 to 7, preferably in the range from 2 to 6 and particularly preferably 3 to 5, and
z denotes 0, 1, 2, 3 or 4, preferably 0 or 2.

The compounds of formula II-1 are preferably selected from the group of the compounds of the formulae II-1a to II-1e:

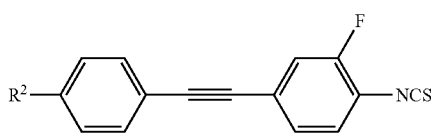

II-1a

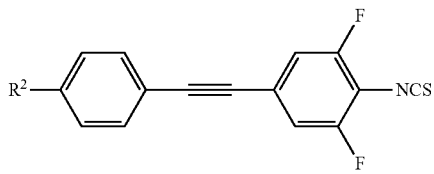

II-1b

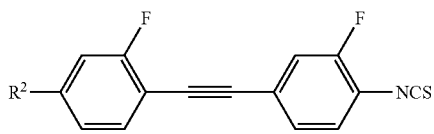

II-1c

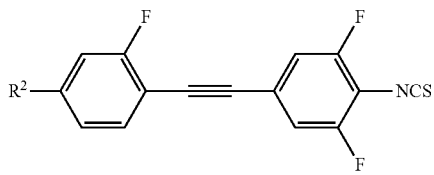

II-1d

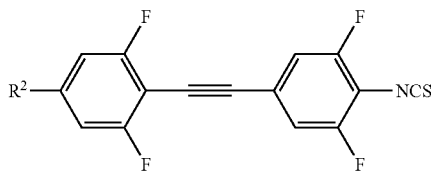

II-1e in which

R² has the meaning indicated above and preferably denotes $C_nH_{2n+1}$ or $CH_2=CH-(CH_2)_z$, and
n denotes an integer in the range from 1 to 7, preferably in the range from 2 to 6 and particularly preferably 3 to 5, and
z denotes 0, 1, 2, 3 or 4, preferably 0 or 2.

The compounds of formula II-2 are preferably selected from the group of the compounds of the formulae II-2a and II-2b:

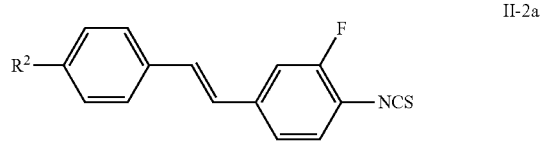

II-2a

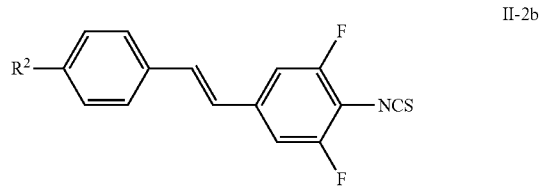

II-2b in which

R² has the meaning indicated above and preferably denotes $C_nH_{2n+1}$ or $CH_2=CH-(CH_2)_z$,
n denotes an integer in the range from 1 to 7, preferably in the range from 2 to 6 and particularly preferably 3 to 5, and
z denotes 0, 1, 2, 3 or 4, preferably 0 or 2.

The compounds of formula II-3 are preferably selected from the group of the compounds of the of formulae II-3a to II-3d:

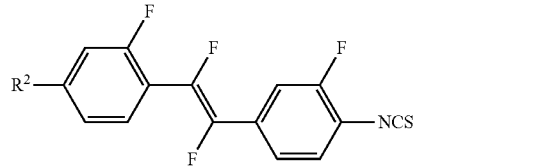

II-3a

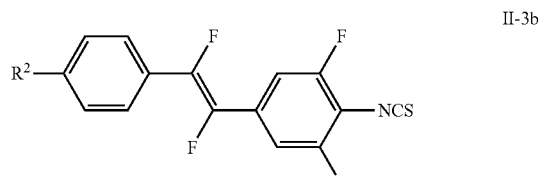

II-3b

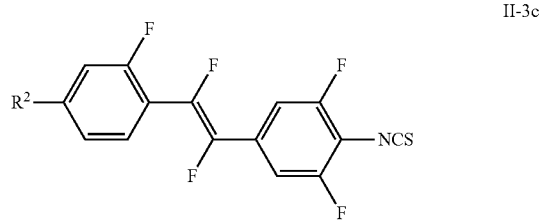

II-3c

-continued

II-3d

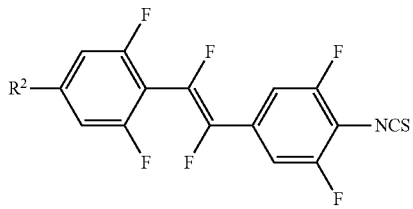

in which

R² has the meaning indicated above and preferably denotes $C_nH_{2n+1}$ or $CH_2=CH-(CH_2)_z$, n denotes an integer in the range from 1 to 7, preferably in the range from 2 to 6 and particularly preferably 3 to 5, and z denotes 0, 1, 2, 3 or 4, preferably 0 or 2.

The compounds of formula III are preferably selected from the group of the compounds of the formulae III-1 to III-6, more preferably of the formulae selected from the group of the compounds of the formulae III-1, III-2, III-3 and III-4, and particularly preferably of formula III-1:

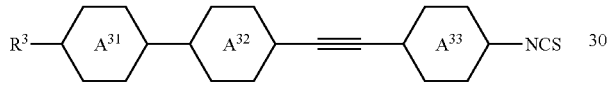
III-1

III-2

III-3

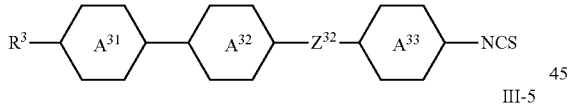
III-4

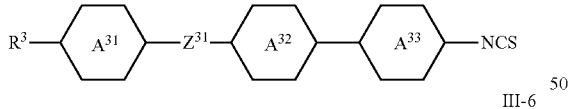
III-5

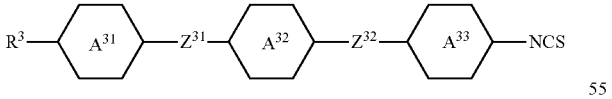
III-6 in which $Z^{31}$ and $Z^{32}$ independently of one another denote trans-CH=CH— or trans-CF=CF—, preferably trans-CH=CH—, and in formula III-6 alternatively one of $Z^{31}$ and $Z^{32}$ may denote —C≡C— and the other groups have the meaning given above under formula III, and preferably R³ denotes non-fluorinated alkyl or alkoxy having 1 to 7 C atoms or non-fluorinated alkenyl having 2 to 7 C atoms, and one of

to

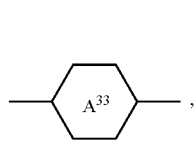

preferably

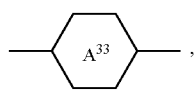

denotes

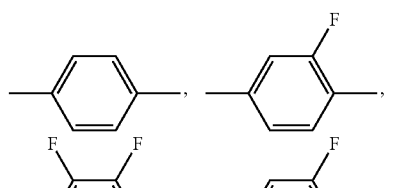

very preferably

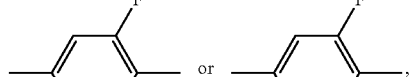

and the others, independently of one another, denote

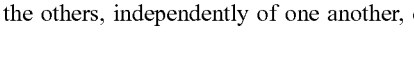

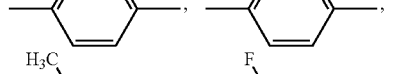

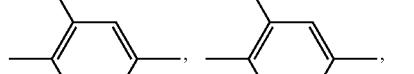

-continued

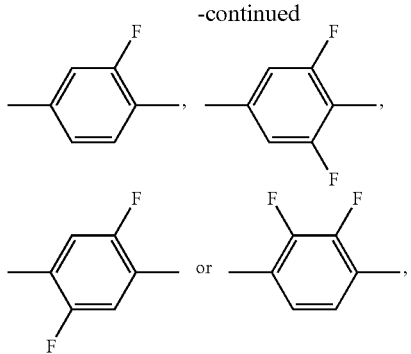

preferably

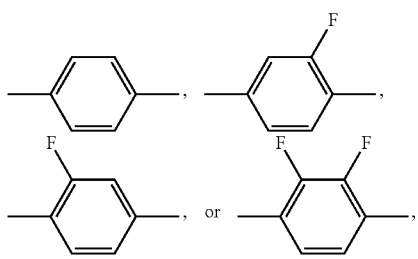

more preferably

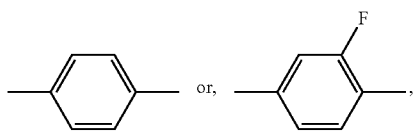

where

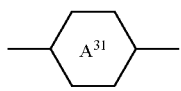

alternatively denotes

and preferably

R³ denotes $C_nH_{2n+1}$ or $CH_2=CH-(CH_2)_z$, n denotes an integer in the range from 1 to 7, preferably in the range from 2 to 6 and particularly preferably 3 to 5, and z denotes 0, 1, 2, 3 or 4, preferably 0 or 2.

The compounds of formula III-1 are preferably selected from the group of the compounds of the formulae III-1a to III-1j, more preferably selected from the group of the compounds of the formulae III-1a, III-1b, III-1g and III-1h, particularly preferably of formula III-1b and/or III-1h:

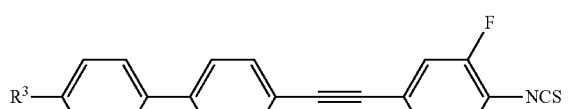
III-1a

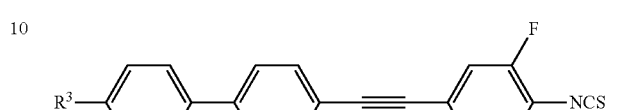
III-1b

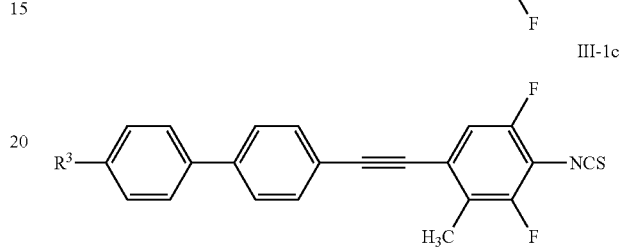
III-1c

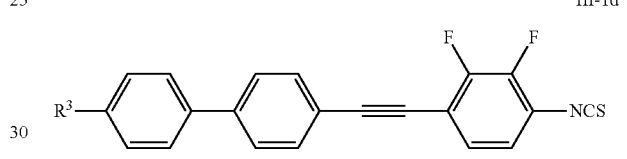
III-1d

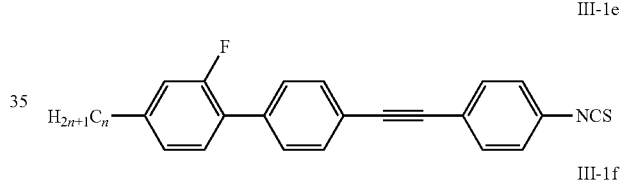
III-1e

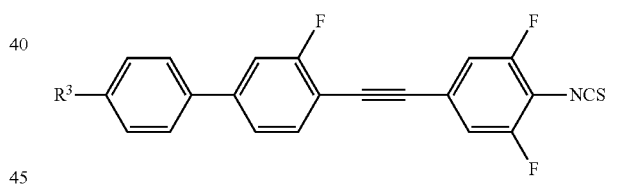
III-1f

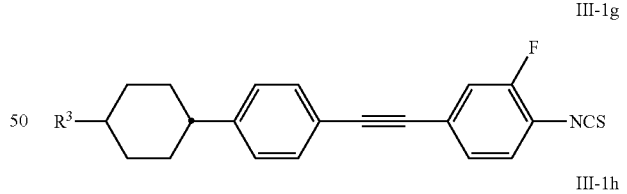
III-1g

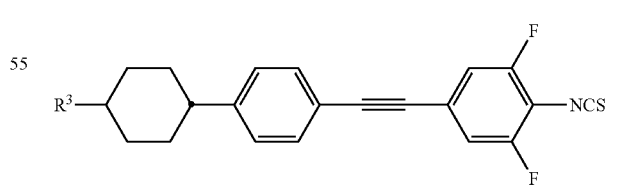
III-1h

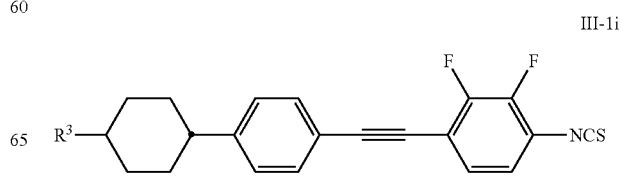
III-1i

III-1j
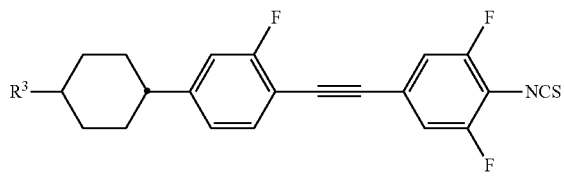

III-2g
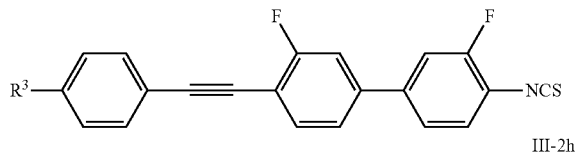

in which
R³ has the meaning indicated above and preferably denotes $C_nH_{2n+1}$ or $CH_2=CH-(CH_2)_z$,
n denotes an integer in the range from 1 to 7, preferably in the range from 2 to 6 and particularly preferably 3 to 5, and
z denotes 0, 1, 2, 3 or 4, preferably 0 or 2.

The compounds of formula III-2 are preferably compounds of formula III-2a to III-2l, very preferably III-2b and/or III-2j:

III-2a
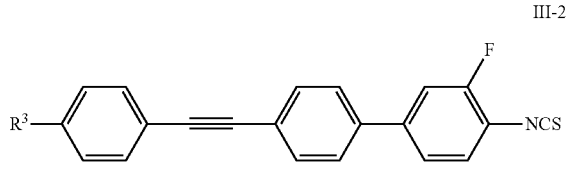

III-2h
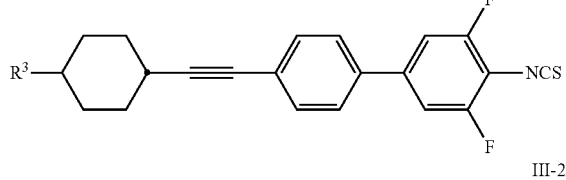

III-2b
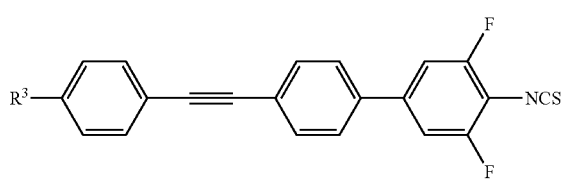

III-2i
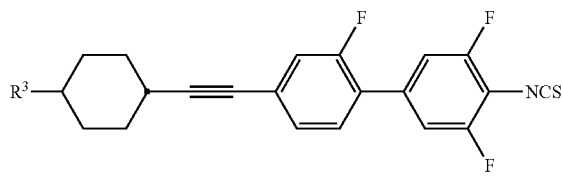

III-2c
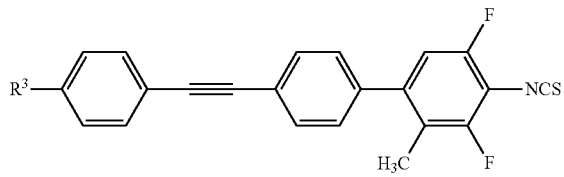

III-2d
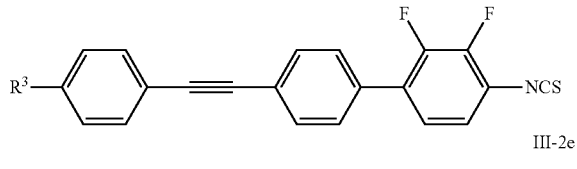

III-2e
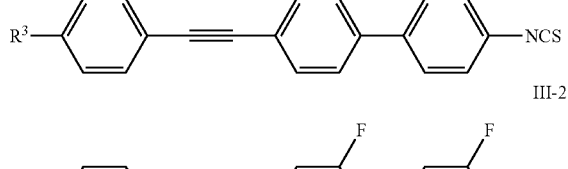

III-2f
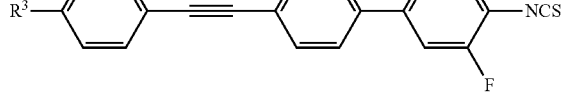

III-2j

III-2k

III-2l in which
R³ has the meaning indicated above and preferably denotes $C_nH_{2n+1}$ or $CH_2=CH-(CH_2)_z$,
n denotes an integer in the range from 1 to 7, preferably in the range from 2 to 6 and particularly preferably 3 to 5, and
z denotes 0, 1, 2, 3 or 4, preferably 0 or 2.

The compounds of formula III-5 are preferably selected from the compounds of formula III-5a:

III-5a
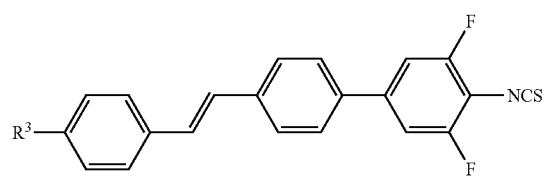

R³ has the meaning indicated above for formula III-5 and preferably denotes $C_nH_{2n+1}$, in which n denotes an integer in the range from 1 to 7, preferably in the range from 2 to 6.

Additionally, the liquid-crystalline media according to the present invention in a certain embodiment, which may be the same or different from the previous preferred embodiments preferably comprise one or more compounds of formula IV,

in which

denotes

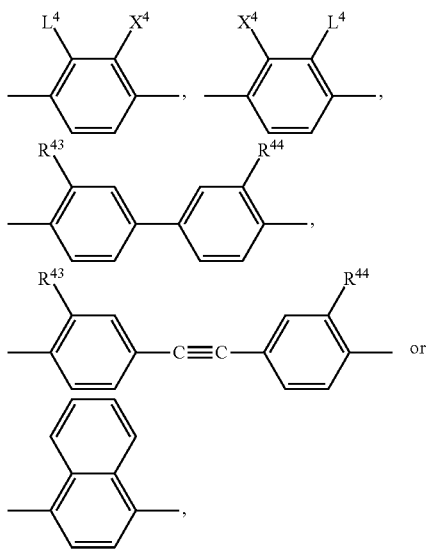

s is 0 or 1, preferably 1, and preferably

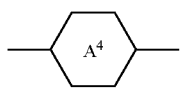

denotes

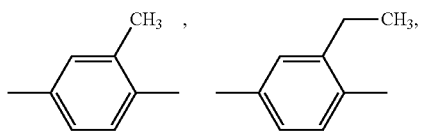

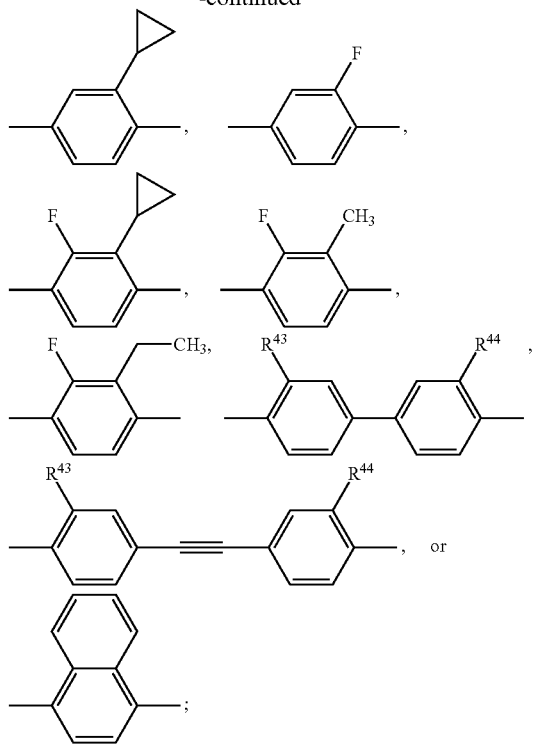

particularly preferably

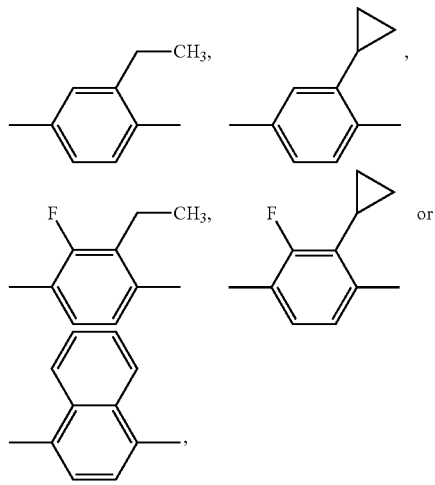

L⁴ denotes H or alkyl having 1 to 6 C atoms, cycloalkyl having 3 to 6 C atoms or cycloalkenyl having 4 to 6 C atoms, preferably $CH_3$, $C_2H_5$, n-$C_3H_7$, i-$C_3H_7$, cyclopropyl, cyclobutyl, cyclohexyl, cyclopent-1-enyl or cyclohex-1-enyl, and particularly preferably $CH_3$, $C_2H_5$, cyclopropyl or cyclobutyl, X⁴ denotes H, alkyl having 1 to 3 C atoms or halogen, preferably H, F or Cl, more preferably H or F and very particularly preferably F, R⁴¹ to R⁴⁴, independently of one another, denote non-fluorinated alkyl or non-fluorinated alkoxy, each having 1 to 15 C atoms, non-fluorinated alkenyl, non-fluorinated alkenyloxy or non-fluorinated alkoxyalkyl, each having 2 to 15 C atoms, or cycloalkyl, alkylcycloalkyl, cycloalkenyl, alkylcycloalkenyl, alkylcycloalkylalkyl or alkylcycloalkenylalkyl, each having up to 15 C atoms, and alternatively one of $R^{43}$ and $R^{44}$ or both also denote H, preferably $R^{41}$ and $R^{42}$, independently of one another, denote non-fluorinated alkyl or non-fluorinated alkoxy, each having 1 to 7 C atoms, or non-fluorinated alkenyl, non-fluorinated alkenyloxy or non-fluorinated alkoxyalkyl, each having 2 to 6 C atoms, particularly preferably $R^{41}$ denotes non-fluorinated alkyl having 1 to 7 C atoms or non-fluorinated alkenyl, non-fluorinated alkenyloxy or non-fluorinated alkoxyalkyl, each having 2 to 6 C atoms, and particularly preferably $R^{42}$ denotes non-fluorinated alkyl or non-fluorinated alkoxy, each having 1 to 7 C atoms, and preferably $R^{43}$ and $R^{44}$ denote H, non-fluorinated alkyl having 1 to 5 C atoms, non-fluorinated cycloalkyl or cycloalkenyl having 3 to 7 C atoms, non-fluorinated alkylcyclohexyl or non-fluorinated cyclohexylalkyl, each having 4 to 12 C atoms, or non-fluorinated alkylcyclohexylalkyl having 5 to 15 C atoms, particularly preferably cyclopropyl, cyclobutyl or cyclohexyl, and very particularly preferably at least one of $R^{43}$ and $R^{44}$ denotes n-alkyl, particularly preferably methyl, ethyl or n-propyl, and the other denotes H or n-alkyl, particularly preferably H, methyl, ethyl or n-propyl.

Very preferably, the compounds of formula IV are selected from the compounds of the formula IV-1

IV-1

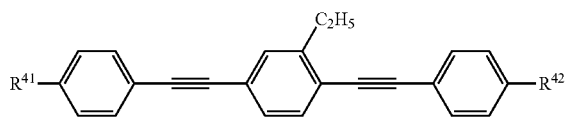

in which $R^{41}$ and $R^{42}$, identically or differently, denote alkyl having 2, 3, 4, 5 or 6 C atoms.

As used herein, the expression dielectrically positive describes compounds or components where $\Delta\varepsilon > 3.0$, dielectrically neutral describes those where $-1.5 \leq \Delta\varepsilon \leq 3.0$ and dielectrically negative describes those where $\Delta\varepsilon < -1.5$. $\Delta\varepsilon$ is determined at a frequency of 1 kHz and at 20° C. The dielectric anisotropy of the respective compound is determined from the results of a solution of 10% of the respective individual compound in a nematic host mixture. If the solubility of the respective compound in the host mixture is less than 10%, the concentration is reduced to 5%. The capacitances of the test mixtures are determined both in a cell having homeotropic alignment and in a cell having homogeneous alignment. The cell thickness of both types of cells is approximately 20 μm. The voltage applied is a rectangular wave having a frequency of 1 kHz and an effective value of typically 0.5 V to 1.0 V, but it is always selected to be below the capacitive threshold of the respective test mixture.

$\Delta\varepsilon$ is defined as $(\varepsilon_\| - \varepsilon_\perp)$, while $\varepsilon_{ave.}$ is $(\varepsilon_\| + 2\varepsilon_\perp)/3$.

The host mixture used for the determination of physical constants of pure compounds by extrapolation is ZLI-4792 from Merck KGaA, Germany. The absolute values of the dielectric constants, the birefringence ($\Delta n$) and the rotational viscosity ($\gamma_1$) of the compounds are determined from the change in the respective values of the host mixture on addition of the compounds. The concentration in the host is 10% or in case of insufficient solubility 5%. The values are extrapolated to a concentration of 100% of the added compounds.

In the examples, the phase sequences of pure compounds are given using the following abbreviations:

K: crystalline, N: nematic, SmA: smectic A, SmB: smectic B, I: isotropic.

Components having a nematic phase at the measurement temperature of 20° C. are measured as such, all others are treated like compounds.

The expression threshold voltage in the present application refers to the optical threshold and is quoted for 10% relative contrast ($V_{10}$), and the expression saturation voltage refers to the optical saturation and is quoted for 90% relative contrast ($V_{90}$), in both cases unless expressly stated otherwise. The capacitive threshold voltage ($V_0$), also called the Freedericks threshold ($V_{Fr}$), is only used if expressly mentioned.

The parameter ranges indicated in this application all include the limit values, unless expressly stated otherwise.

The different upper and lower limit values indicated for various ranges of properties in combination with one another give rise to additional preferred ranges.

Throughout this application, the following conditions and definitions apply, unless expressly stated otherwise. All concentrations are quoted in percent by weight and relate to the respective mixture as a whole, all temperatures are quoted in degrees Celsius and all temperature differences are quoted in differential degrees. All physical properties are determined in accordance with "Merck Liquid Crystals, Physical Properties of Liquid Crystals", Status November 1997, Merck KGaA, Germany, and are quoted for a temperature of 20° C., unless expressly stated otherwise. The optical anisotropy ($\Delta n$) is determined at a wavelength of 589.3 nm. The dielectric anisotropy ($\Delta\varepsilon$) is determined at a frequency of 1 kHz. The threshold voltages, as well as all other electro-optical properties, are determined using test cells produced at Merck KGaA, Germany. The test cells for the determination of $\Delta\varepsilon$ have a cell thickness of approximately 20 μm. The electrode is a circular ITO electrode having an area of 1.13 cm² and a guard ring. The orientation layers are SE-1211 from Nissan Chemicals, Japan, for homeotropic orientation ($\varepsilon_\|$) and polyimide AL-1054 from Japan Synthetic Rubber, Japan, for homogeneous orientation ($\varepsilon_\perp$). The capacitances are determined using a Solatron 1260 frequency response analyzer using a sine wave with a voltage of 0.3 $V_{ms}$. The light used in the electro-optical measurements is white light. A set-up using a commercially available DMS instrument from Autronic-Melchers, Germany, is used here. The characteristic voltages have been determined under perpendicular observation. The threshold ($V_{10}$), mid-grey ($V_{50}$) and saturation ($V_{90}$) voltages have been determined for 10%, 50% and 90% relative contrast, respectively.

The liquid-crystalline media are investigated with respect to their properties in the microwave frequency range as described in A. Penirschke et al. "Cavity Perturbation Method for Characterization of Liquid Crystals up to 35 GHz", 34th European Microwave Conference—Amsterdam, pp. 545-548. Compare in this respect also A. Gaebler et al. "Direct Simulation of Material Permittivities . . . ", 12MTC 2009—International Instrumentation and Measurement Technology Conference, Singapore, 2009 (IEEE), pp. 463-

467, and DE 10 2004 029 429 A, in which a measurement method is likewise described in detail.

The liquid crystal is introduced into a polytetrafluoroethylene (PTFE) or quartz capillary. The capillary has an inner diameter of 0.5 mm and an outer diameter of 0.78 mm. The effective length is 2.0 cm. The filled capillary is introduced into the center of the cylindrical cavity with a resonance frequency of 19 GHz. This cavity has a length of 11.5 mm and a radius of 6 mm. The input signal (source) is then applied, and the frequency depending response of the cavity is recorded using a commercial vector network analyzer (N5227A PNA Microwave Network Analyzer, Keysight Technologies Inc. USA. For other frequencies, the dimensions of the cavity are adapted correspondingly.

The change in the resonance frequency and the Q factor between the measurement with the capillary filled with the liquid crystal and the measurement without the capillary filled with the liquid crystal is used to determine the dielectric constant and the loss angle at the corresponding target frequency by means of equations 10 and 11 in the above-mentioned publication A. Penirschke et al., 34$^{th}$ European Microwave Conference—Amsterdam, pp. 545-548, as described therein.

The values for the components of the properties perpendicular and parallel to the director of the liquid crystal are obtained by alignment of the liquid crystal in a magnetic field. To this end, the magnetic field of a permanent magnet is used. The strength of the magnetic field is 0.35 tesla.

In the present application, the term compounds is taken to mean both one compound and a plurality of compounds, unless expressly stated otherwise.

The dielectric anisotropy in the microwave range is defined as $$\Delta\varepsilon_r = (\varepsilon_{r,\parallel} - \varepsilon_{r,\perp}).$$

The tunability ($\tau$) is defined as $$\tau = (\Delta\varepsilon_r / \varepsilon_{r,\parallel}).$$

The material quality ($\eta$) is defined as $$\eta = (\tau / \tan \delta_{\varepsilon r,max}), \text{ where}$$

the maximum dielectric loss is $$\tan \delta_{\varepsilon r,max} = \max\{\tan \delta_{\varepsilon r,\perp}; \tan \delta_{\varepsilon r,\parallel}\}.$$

The liquid crystals employed are either individual substances or mixtures. They preferably have a nematic phase.

All mixtures according to the invention are nematic. The liquid-crystal media according to the invention preferably have nematic phases in preferred ranges given above. The expression have a nematic phase here means on the one hand that no smectic phase and no crystallization are observed at low temperatures at the corresponding temperature and on the other hand that no clearing occurs on heating from the nematic phase. At high temperatures, the clearing point is measured in capillaries by conventional methods. The investigation at low temperatures is carried out in a flow viscometer at the corresponding temperature and checked by storage of bulk samples: The storage stability in the bulk (LTS) of the media according to the invention at a given temperature T is determined by visual inspection. 2 g of the media of interest are filled into a closed glass vessel (bottle) of appropriate size placed in a refrigerator at a predetermined temperature. The bottles are checked at defined time intervals for the occurrence of smectic phases or crystallization. For every material and at each temperature two bottles are stored. If crystallization or the appearance of a smectic phase is observed in at least one of the two correspondent bottles the test is terminated and the time of the last inspection before the one at which the occurrence of a higher ordered phase is observed is recorded as the respective storage stability. The test is finally terminated after 1000 h, i.e. an LTS value of 1000 h means that the mixture is stable at the given temperature for at least 1000 h.

The liquid-crystal media in accordance with the present invention may comprise further additives and chiral dopants in the usual concentrations. The total concentration of these further constituents is in the range from 0% to 10%, preferably 0.1% to 6%, based on the mixture as a whole. The concentrations of the individual compounds used are each preferably in the range from 0.1% to 3%. The concentration of these and similar additives is not taken into consideration when quoting the values and concentration ranges of the liquid-crystal components and liquid-crystal compounds of the liquid-crystal media in this application.

Optionally the media according to the present invention may comprise further liquid crystal compounds in order to adjust the physical properties. Such compounds are known to the skilled person. Their concentration in the media according to the instant invention is preferably 0% to 30%, more preferably 0.1% to 20% and most preferably 1% to 15%.

The liquid-crystal media according to the invention consist of a plurality of compounds, preferably 3 to 30, more preferably 4 to 20 and very preferably 4 to 16 compounds. These compounds are mixed in a conventional manner. In general, the desired amount of the compound used in the smaller amount is dissolved in the compound used in the larger amount. If the temperature is above the clearing point of the compound used in the higher concentration, it is particularly easy to observe completion of the dissolution process. It is, however, also possible to prepare the media in other conventional ways, for example using so-called pre-mixes, which can be, for example, homologous or eutectic mixtures of compounds, or using so-called "multi bottle" systems, the constituents of which are themselves ready-to-use mixtures.

All temperatures, such as, for example, the melting point T(C,N) or T(C,S), the transition from the smectic (S) to the nematic (N) phase T(S,N) and the clearing point T(N,I) of the liquid crystals, are quoted in degrees Celsius. All temperature differences are quoted in differential degrees.

Herein, the structures of the mesogenic compounds are indicated by means of abbreviations, also referred to as acronyms. In these acronyms, the chemical formulae are abbreviated as follows using Tables A to C below. All groups $C_nH_{2n+1}$, $C_mH_{2m+1}$ and $C_lH_{2l+1}$, and $C_nH_{2n-1}$, $C_mH_{2m-1}$ and $C_lH_{2l-1}$ denote straight-chain alkyl or alkylene, respectively, in each case having n, m or l C atoms, wherein n and m, independently are 1, 2, 3, 4, 5, 6 or 7 and l is 1, 2 or 3. Table A lists the codes used for the ring elements of the core structures of the compounds, while Table B shows the linking groups and end groups. Table C shows illustrative structures of compounds with their respective abbreviations.

TABLE A

Ring elements

C 

TABLE A-continued
| Ring elements | | |
|---|---|---|
| D | 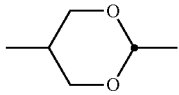 | |
| DI | 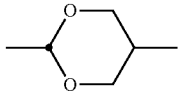 | |
| A | 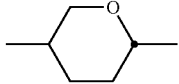 | |
| AI | 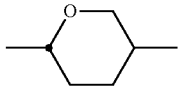 | |
| G | 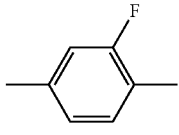 | |
| GI | 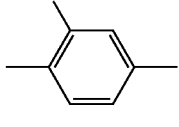 | |
| G(1) | 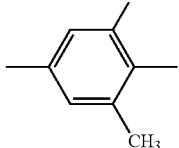 | |
| G(1)I | 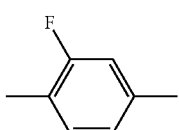 | |
| G(Cl) | 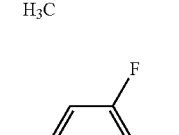 | |
| P(Cl,Cl) | 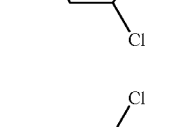 | |
| GI(Cl) | 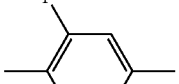 | |
| P(Cl,Cl)I |  | |
| U | 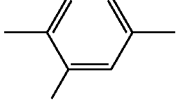 | |
| UI | 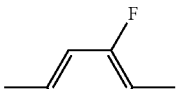 | |
| U(F,F) | 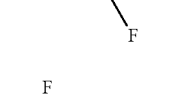 | |
| Y | 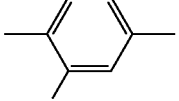 | |
| M | 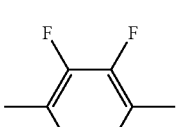 | |
| MI | 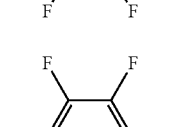 | |
| N | 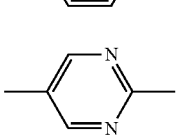 | |
| NI | 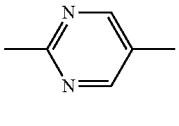 | |

TABLE A-continued

| Ring elements | |
|---|---|
| Np | (2,6-naphthalene) |
| N3f | (naphthalene with 3 F substituents) |
| N3fI | (naphthalene with 3 F substituents, isomer) |
| tH | (tetrahydronaphthalene) |
| tHI | (tetrahydronaphthalene, isomer) |
| tH2f | (tetrahydronaphthalene with 2 F) |
| tH2fI | (tetrahydronaphthalene with 2 F, isomer) |
| dH | (decahydronaphthalene) |
| K | (indane with F substituents) |
| KI | (indane with F substituents, isomer) |
| L | (cyclohexylene) |
| Ll | (cyclohexenylene) |
| F | (fluoro-cyclohexene) |
| Fl | (fluoro-cyclohexene, isomer) |
| P | (phenylene) |
| P(n,m) | (phenylene with $C_nH_{2n+1}$ and $C_mH_{2m+1}$) |
| P(o) | (phenylene with $C_oH_{2o+1}$) |
| Pl(o) | (phenylene with $C_oH_{2o+1}$, isomer) |
| P(i3) | (phenylene with isopropyl) |
| Pl(ic3) | (phenylene with isopropyl, isomer) |
| P(t4) | (phenylene with tert-butyl) |

TABLE A-continued
Ring elements
| | |
|---|---|
| Pt(t4) | 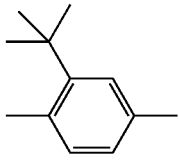 |
| P(c3) | 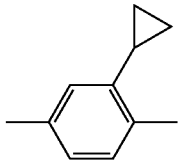 |
| Pl(c3) | 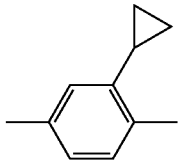 |
| P(c4) | 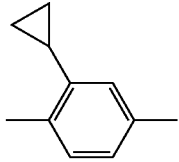 |
| Pl(c4) | 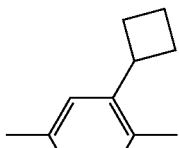 |
| P(c5) | 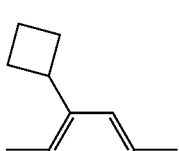 |
| Pl(c5) | 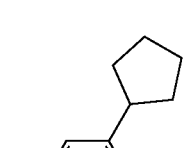 |
| P(e5) | 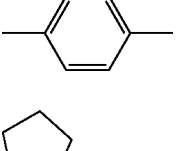 |
| Pl(e5) | 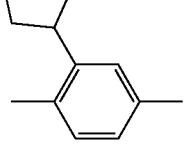 |
| P(c6) | 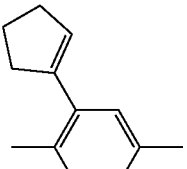 |
| Pl(c6) | 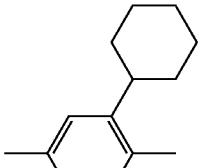 |
| P(e6) | 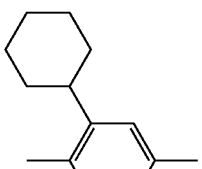 |
| Pl(e6) | 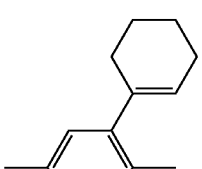 |
| Gl(o) | 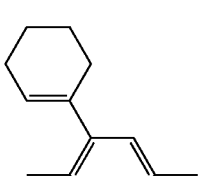 |
in which o = 1, 2, 3, 4, 5 or 6
| | |
|---|---|
| G(o) | 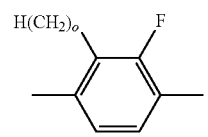 |
in which o = 1, 2, 3, 4, 5 or 6
| | |
|---|---|
| Gl(i3) | 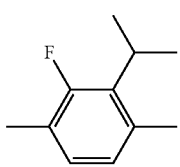 |

TABLE A-continued
| Ring elements | |
|---|---|
| G(i3) | 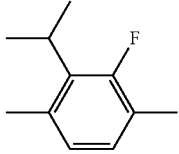 |
| GI(t4) | 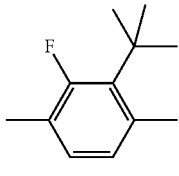 |
| G(t4) | 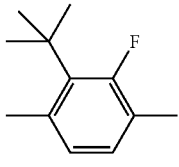 |
| GI(c3) | 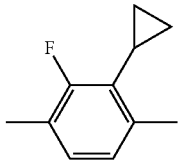 |
| G(c3) | 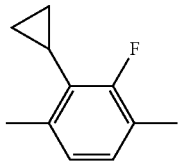 |
| GI(c4) | 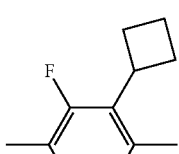 |
| G(c4) | 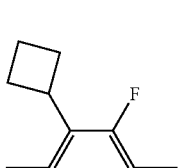 |
| GI(c5) | 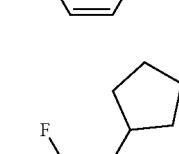 |
| G(c5) | 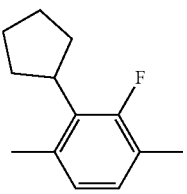 |
| GI(e5) | 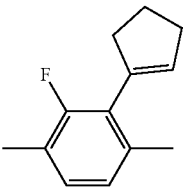 |
| G(e5) | 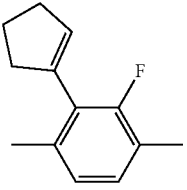 |
| GI(c6) | 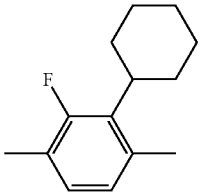 |
| G(c6) | 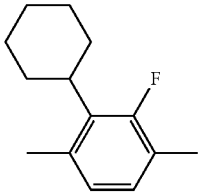 |
| GI(e6) | 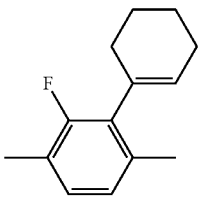 |
| G(e6) | 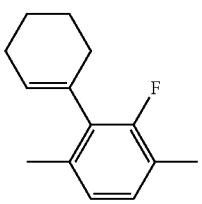 |
| Np(1,4) | 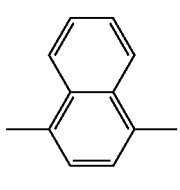 |

TABLE A-continued

Ring elements

| | |
|---|---|
| Th | (thienothiophene structure) |

TABLE B

Linking groups

| | | | |
|---|---|---|---|
| E | —CH$_2$CH$_2$— | Z | —CO—O— |
| V | —CH=CH— | ZI | —O—CO— |
| X | —CF=CH— | O | —CH$_2$—O— |
| XI | —CH=CF— | OI | —O—CH$_2$— |
| B | —CF=CF— | Q | —CF$_2$—O— |
| T | —C≡C— | QI | —O—CF$_2$— |
| W | —CF$_2$CF$_2$— | | | in which n and m each denote integers, and the three dots "..." are placeholders for other abbreviations from this table.

Branched lateral groups are numbered starting from the position next to the ring (1) where the longest chain is selected, the smaller number indicating the length of the branch and the superscript number in brackets indicates the position of the branch, for example:

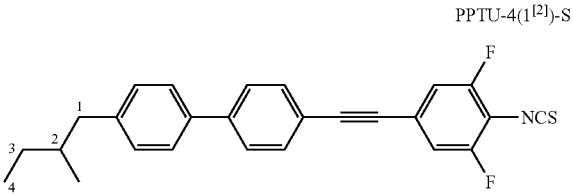

PPTU-4(1[2])-S

TABLE B

End groups

| | | | |
|---|---|---|---|
| Left-hand side | | Right-hand side / Used alone | |
| -n- | C$_n$H$_{2n+1}$— | -n | —C$_n$H$_{2n+1}$ |
| -nO- | C$_n$H$_{2n+1}$—O— | -On | —O—C$_n$H$_{2n+1}$ |
| —V— | CH$_2$=CH— | —V | —CH=CH$_2$ |
| -nV- | C$_n$H$_{2n+1}$—CH=CH— | -nV | —C$_n$H$_{2n}$—CH=CH$_2$ |
| -Vn- | CH$_2$=CH—C$_n$H$_{2n+1}$— | -Vn | —CH=CH—C$_n$H$_{2n+1}$ |
| -nVm- | C$_n$H$_{2n+1}$—CH=CH—C$_m$H$_{2m}$— | -nVm | —CH$_2$N—CH=CH—C$_m$H$_{2m+1}$ |
| —N— | N≡C— | —N | —C≡N |
| —S— | S=C=N— | —S | —N=C=S |
| —F— | F— | —F | —F |
| -CL- | Cl— | -CL | —Cl |
| -M- | CFH$_2$— | -M | —CFH$_2$ |
| -D- | CF$_2$H— | -D | —CF$_2$H |
| -T- | CF$_3$— | -T | —CF$_3$ |
| -MO- | CFH$_2$O— | -OM | —OCFH$_2$ |
| -DO- | CF$_2$HO— | -OD | —OCF$_2$H |
| -TO- | CF$_3$O— | -OT | —OCF$_3$ |
| -FXO- | CF$_2$=CH—O— | -OXF | —O—CH=CF$_2$ |
| -A- | H—C≡C— | -A | —C≡C—H |
| -nA- | C$_n$H$_{2n+1}$—C≡C— | -An | —C≡C—C$_n$H$_{2n+1}$ |
| -NA- | N≡C—C≡C— | -AN | —C≡C—C≡N |
| -(cn)- | (CH$_2$)$_{n-2}$ cyclopropyl | -(cn) | (CH$_2$)$_{n-2}$ cyclopropyl |
| -(cn)m- | (CH$_2$)$_{n-2}$—(CH$_2$)$_m$— | -m(cn) | —(CH$_2$)$_m$—(CH$_2$)$_{n-2}$ |

Used in combination with others

| | | | |
|---|---|---|---|
| -...A...- | —C≡C— | -...A... | —C≡C— |
| -...V...- | —CH=CH— | -...V... | —CH=CH— |
| -...Z...- | —CO—O— | -...Z... | —CO—O— |
| -...ZI...- | —O—CO— | -...ZI.. | —O—CO— |
| -...K... | —CO— | -...K... | —CO— |
| -...W...- | —CF=CF— | -...W.. | —CF=CF— |

-continued

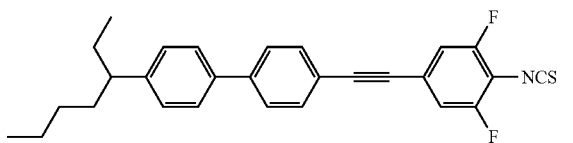

PPTU-5(2[1])-S

The following table shows illustrative structures together with their respective abbreviations. These are shown in order to illustrate the meaning of the rules for the abbreviations. They furthermore represent compounds which are preferably used.

The following illustrative structures are examples as well as compounds, which are preferably additionally used in the media:

TABLE C

Illustrative structures

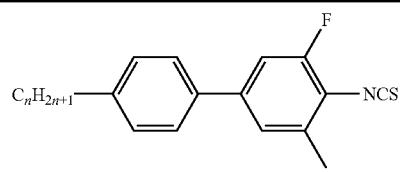

PG(1)-n-S

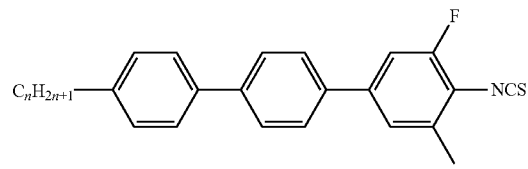

PPG(1)-n-S

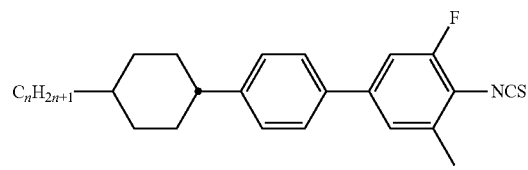

CPG(1)-n-S

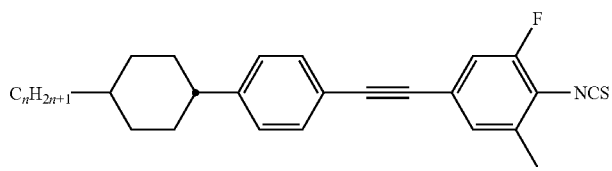

CPTG(1)-n-S

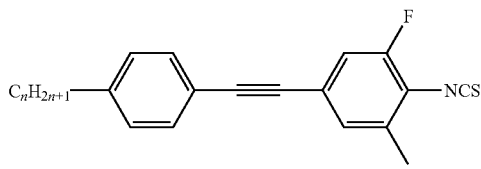

PTG(1)-n-S

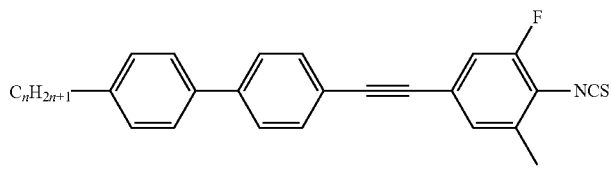

PPTG(1)-n-S

TABLE C-continued
Illustrative structures
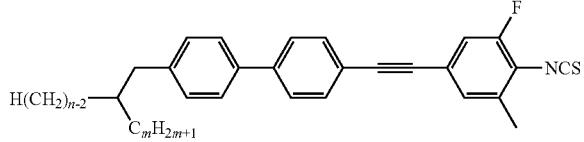
PPTG(1)-n(m[2])-S
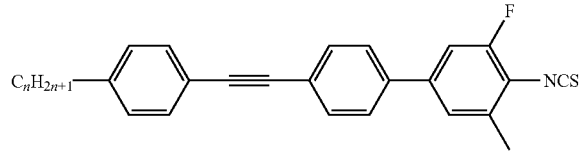
PTPG(1)-n-S
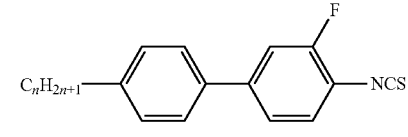
PG-n-S
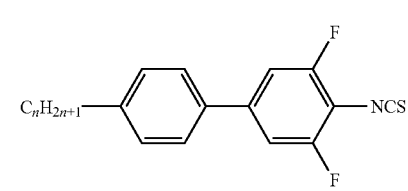
PU-n-S
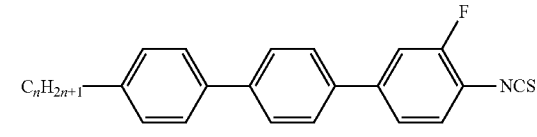
PPG-n-S
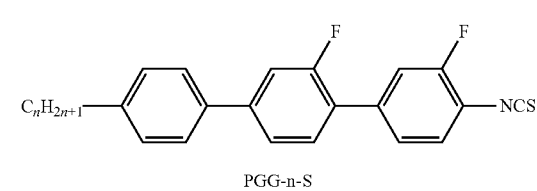
PGG-n-S
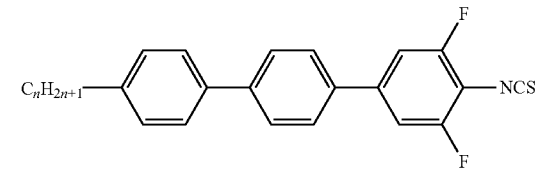
PPU-n-S
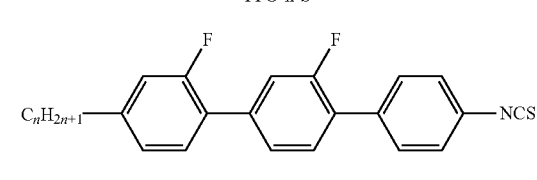
GGP-n-S TABLE C-continued
Illustrative structures
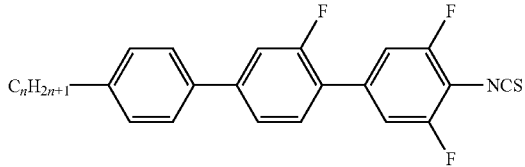
PGU-n-S
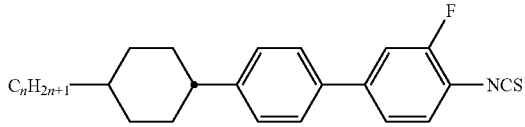
CPG-n-S
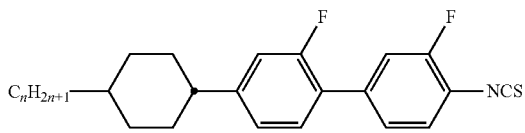
CGG-n-S
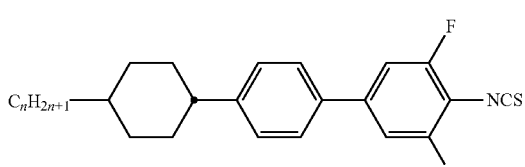
CPU-n-S
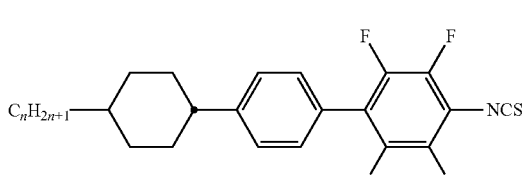
CPU(F,F)-n-S
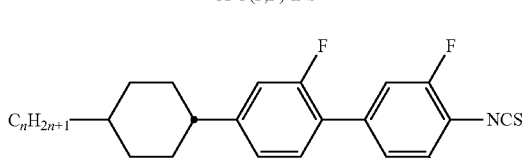
CGU-n-S
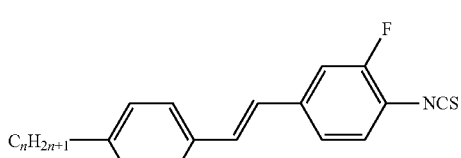
PVG-n-S TABLE C-continued
Illustrative structures
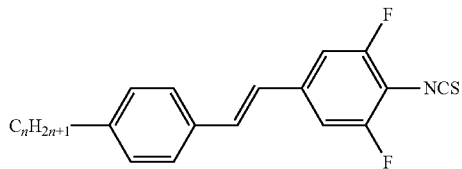
PVU-n-S
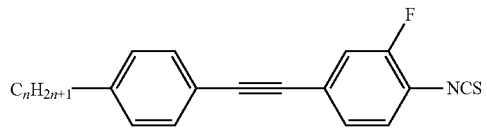
PTG-n-S
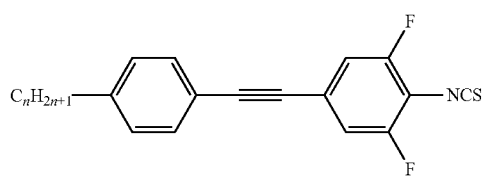
PTU-n-S
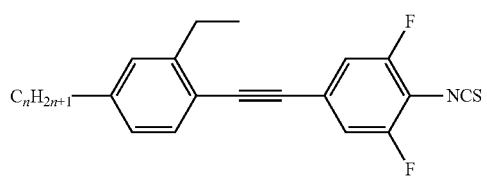
P(2)TU-n-S
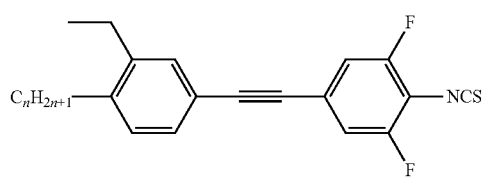
PI(2)TU-n-S
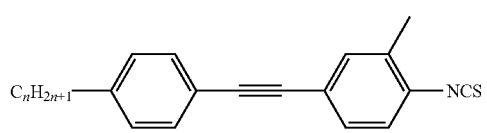
PTP(1)-n-S
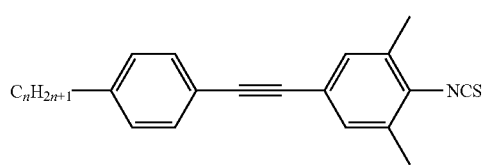
PTP(1,1)-n-S TABLE C-continued
Illustrative structures
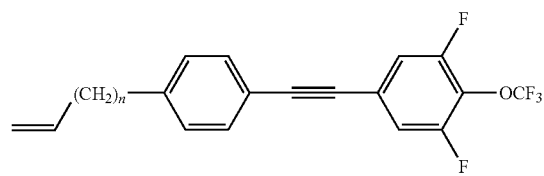
PTU-Vn-OT
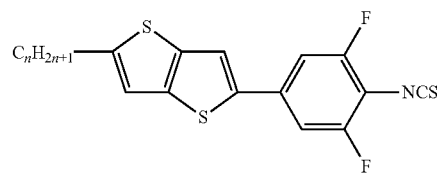
ThU-n-S
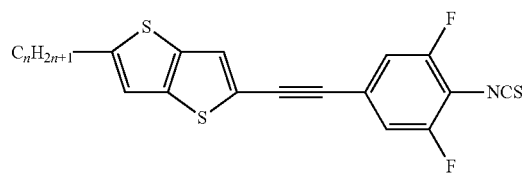
ThTU-n-S
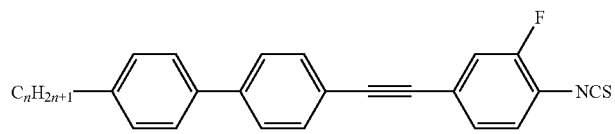
PPTG-n-S
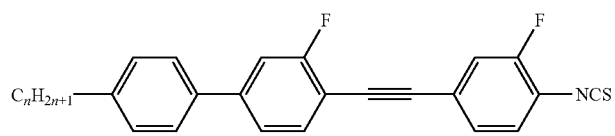
PGTG-n-S
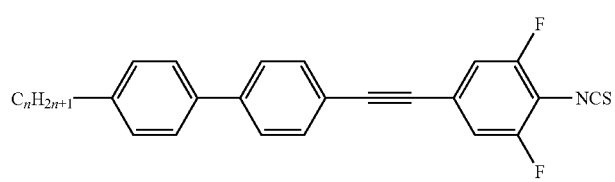
PPTU-n-S
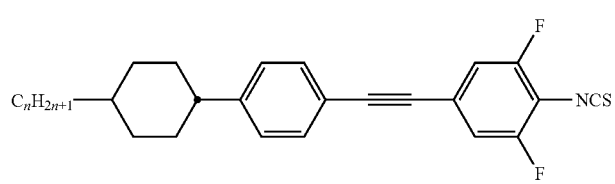
CPTU-n-S TABLE C-continued Illustrative structures PPTU-n(m[2])-S PTPU-n-S PTPG(Cl)-n-S PTPP(Cl,Cl)-n-S PTPI(c3)TU-n-F PTP(2)WU-n-F TABLE C-continued
Illustrative structures
PTPI(2)GU-n-F
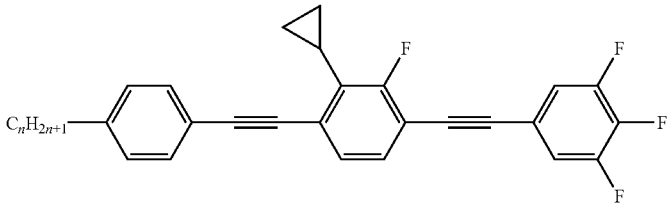
PTG(c3)TU-n-F
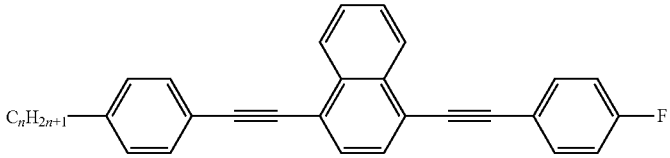
PTN(1,4)TP-n-F
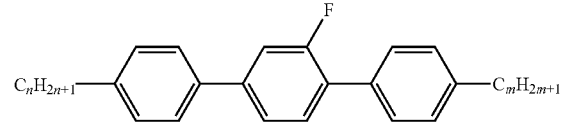
PGP-n-m
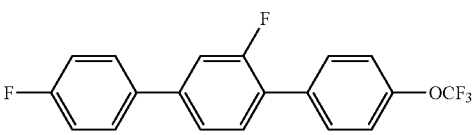 [SMILES: Fc1ccc(-c2ccc(-c3ccc(OC(F)(F)F)cc3)c(F)c2)cc1]
PGP-F-OT
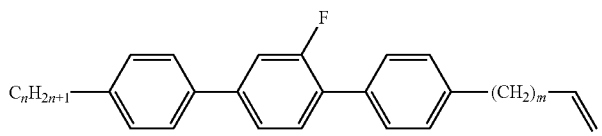
PGP-n-mV
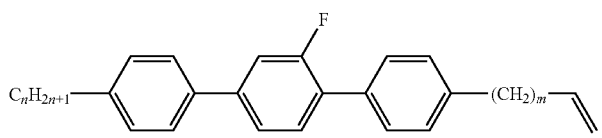
PGP-n-mVI
PYP-n-m
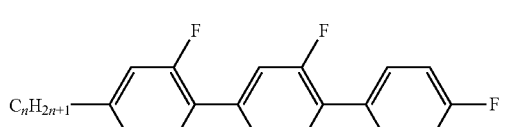
GGP-n-F TABLE C-continued
Illustrative structures
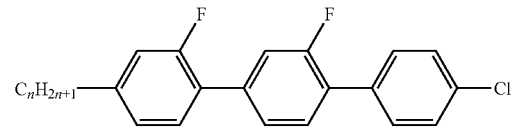
GGP-n-CL
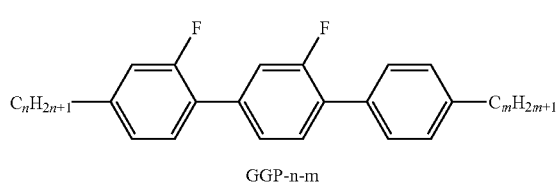
GGP-n-m
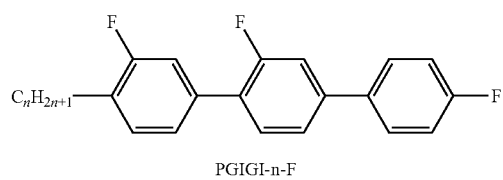
PGIGI-n-F
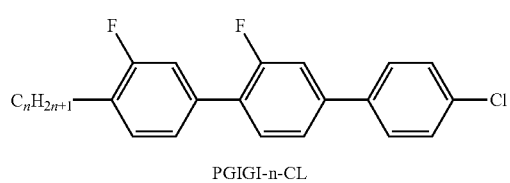
PGIGI-n-CL
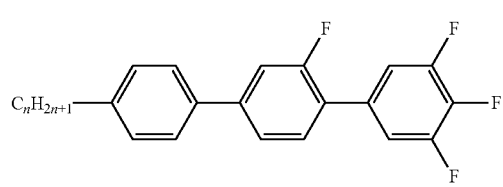
PGU-n-F
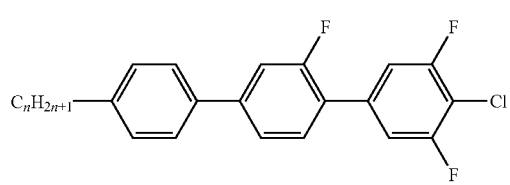
PGU-n-CL
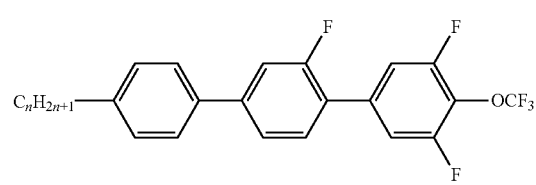
PGU-n-OT
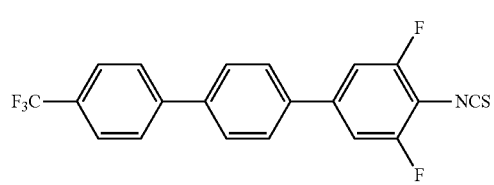

TABLE C-continued
Illustrative structures
PPU-T-S
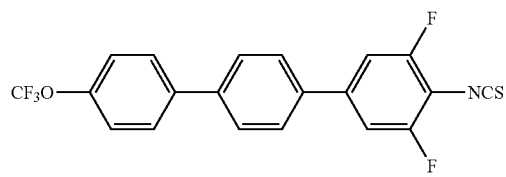
PPU-TO-S
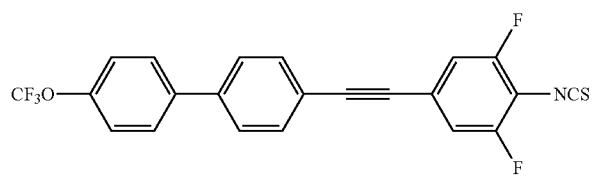
PPTU-TO-S
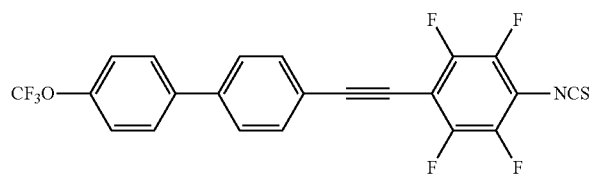
PPTU(F,F)-TO-S
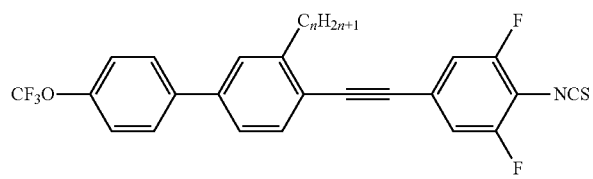
PP(n)TU-TO-S
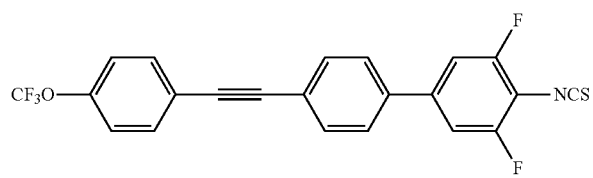
PTPU-TO-S
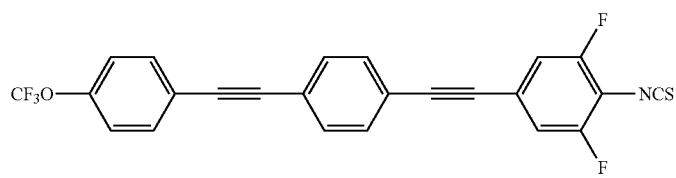
PTPTU-TO-S
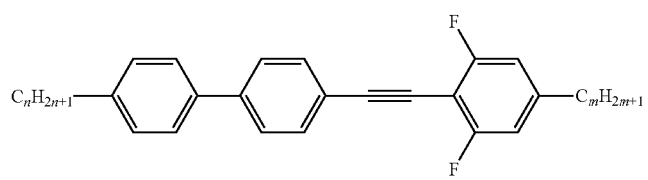
PPTUI-n-m TABLE C-continued
Illustrative structures
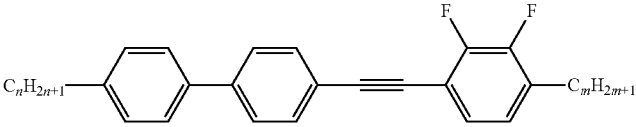
PPTY-n-m
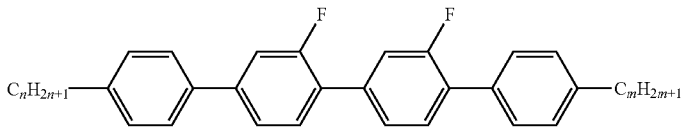
PGGP-n-m
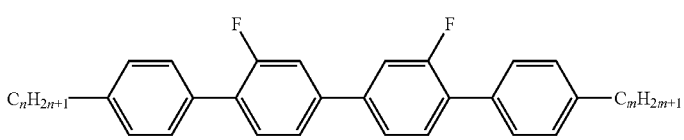
PGIGP-n-m
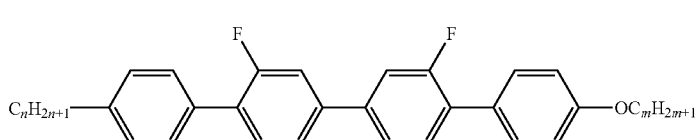
PGIGP-n-Om
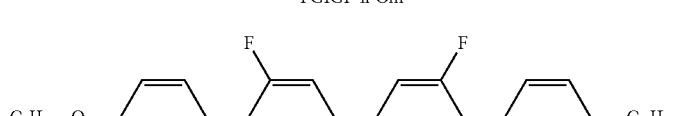
PGIGP-nO-m
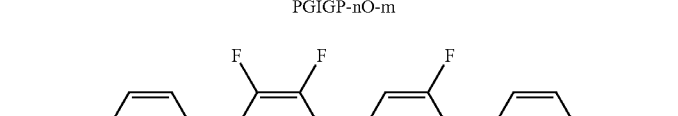
PYGP-n-m
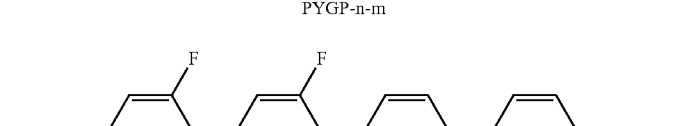
GGPP-n-m
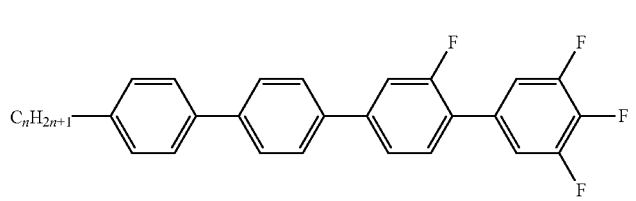
PPGU-n-F TABLE C-continued
Illustrative structures
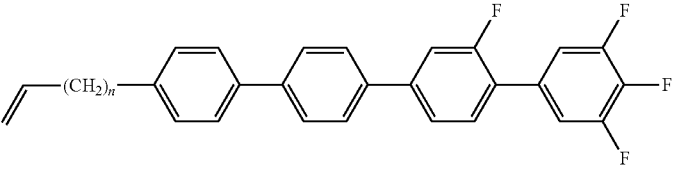
PPGU-Vn-F
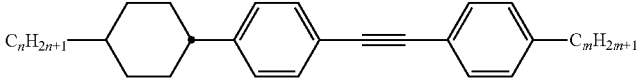
CPTP-n-m
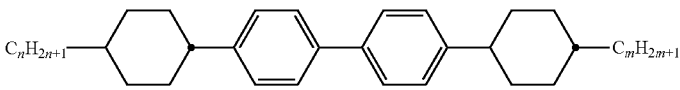
CPPC-n-m
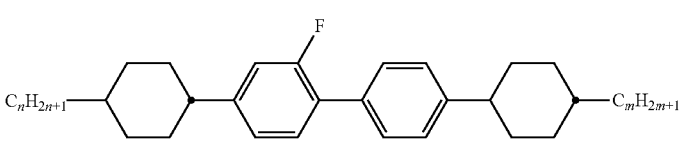
CGPC-n-m
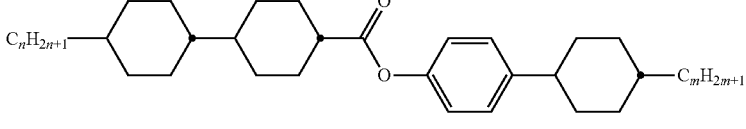
CCZPC-n-m
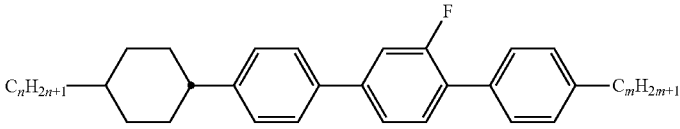
CPGP-n-m
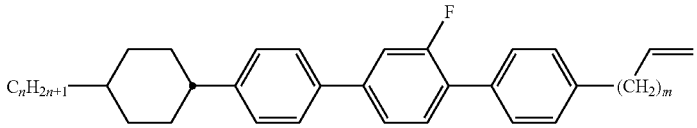
CPGP-n-mV
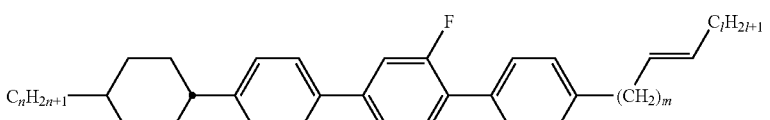
CPGP-n-mVI
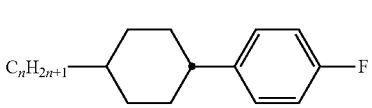

TABLE C-continued
Illustrative structures
CP-n-F
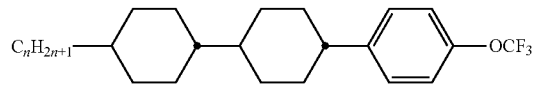
CCP-n-OT
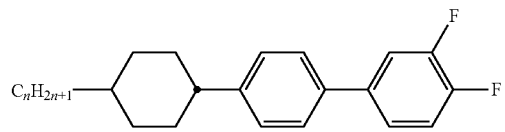
CPG-n-F
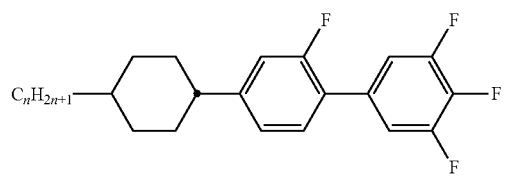
CGU-n-F
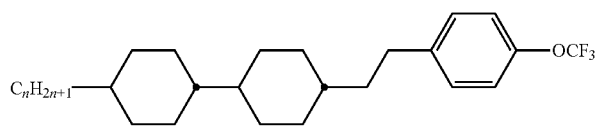
CCEP-n-OT
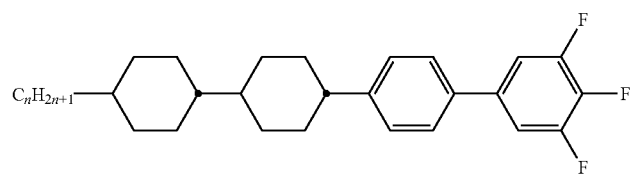
CCPU-n-F
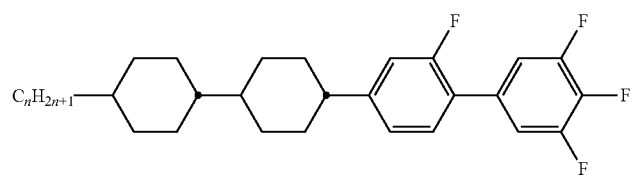
CCGU-n-F
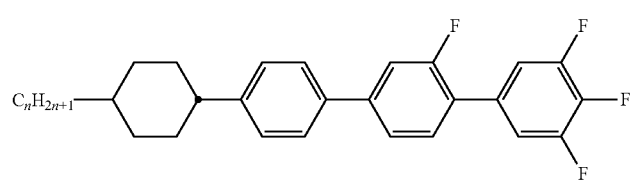
CPGU-n-F TABLE C-continued Illustrative structures

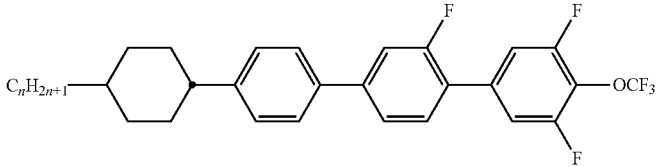

CPGU-n-OT

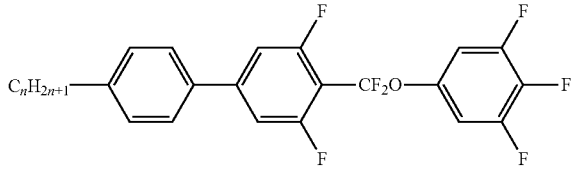

PUQU-n-F

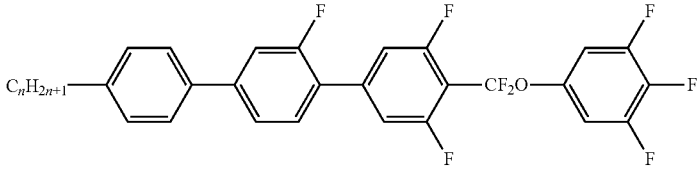

PGUQU-n-F

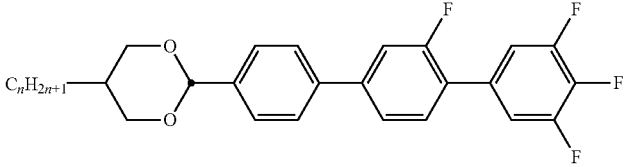

DPGU-n-F

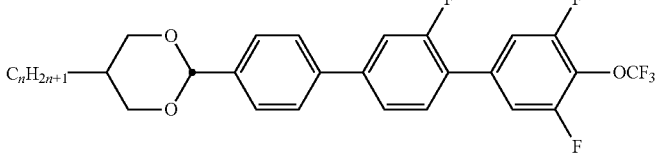

DPGU-n-OT

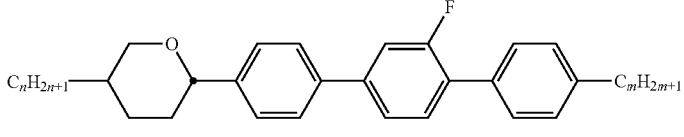

APGP-n-m in which m and n, identically or differently, are 1, 2, 3, 4, 5, 6 or 7.

Preferably, the medium according to the invention comprises one or more compounds selected from the compounds of Table C.

Unless indicated otherwise, parts or percent data denote parts by weight or percent by weight.

Above and below:

$V_o$ denotes threshold voltage, capacitive [V] at 20° C., $n_e$ denotes extraordinary refractive index at 20° C. and 589 nm, $n_o$ denotes ordinary refractive index at 20° C. and 589 nm, $\Delta_n$ denotes optical anisotropy at 20° C. and 589 nm, $\varepsilon_\perp$ denotes dielectric permittivity perpendicular to the director at 20° C. and 1 kHz, $\varepsilon_\parallel$ denotes dielectric permittivity parallel to the director at 20° C. and 1 kHz, $\Delta\varepsilon$ denotes dielectric anisotropy at 20° C. and 1 kHz, cl.p., T(N,I) denotes clearing point [° C.], $\gamma_1$ denotes rotational viscosity measured at 20° C. [mPa·s], $K_1$ denotes elastic constant, "splay" deformation at 20° C. [pN], $K_2$ denotes elastic constant, "twist" deformation at 20° C. [pN], $K_3$ denotes elastic constant, "bend" deformation at 20° C. [pN], $K_{avg.}$ denotes average elastic constant defined as $K_{avg.} = \frac{1}{3}(1.5 \cdot K_1 + K_3)$ LTS denotes low-temperature stability (nematic phase), determined in test cells or in the bulk, as specified.

Unless explicitly noted otherwise, all values indicated in the present application for temperatures, such as, for example, the melting point T(C,N), the transition from the smectic (S) to the nematic (N) phase T(S,N) and the clearing point T(N,I) or cl.p., are indicated in degrees Celsius (° C.). M.p. denotes melting point. Furthermore, Tg=glass state, C=crystalline state, N=nematic phase, S=smectic phase and I=isotropic phase. The numbers between these symbols represent the transition temperatures.

The term "threshold voltage" for the present invention relates to the capacitive threshold ($V_0$), also called the Freedericksz threshold, unless explicitly indicated otherwise. In the examples, as is generally usual, the optical threshold can also be indicated for 10% relative contrast ($V_{10}$).

The display used for measurement of the capacitive threshold voltage consists of two plane-parallel glass outer plates at a separation of 20 µm, which each have on the insides an electrode layer and an unrubbed polyimide alignment layer on top, which cause a homeotropic edge alignment of the liquid-crystal molecules.

The Clearing point is measured using the Mettler Thermosystem FP900. The optical anisotropy (Δn) is measured using an Abbe Refractometer H005 (Natrium-spectral lamp Na10 at 589 nm, 20° C.). The dielectric anisotropy (Δε) is measured using an LCR-Meter E4980A/Agilent (G005) at 20° C. (ε-parallel-cells with JALS 2096-R1). The turn on voltage ($V_0$) is measured using an LCR-Meter E4980A/Agilent (G005) at 20° C. (ε-parallel-cells with JALS 2096-R1). The rotational viscosity ($\gamma_1$) is measured using a TOYO LCM-2 (0002) at 20° C. (gamma 1 negative cells with JALS-2096-R1). The elastic constant ($K_1$, splay) is measured using an LCR-Meter E4980A/Agilent (G005) at 20° C. (ε parallel-cells with JALS 2096-R1). $K_3$: The elastic constant ($K_3$, bend) is measured using an LCR-Meter E4980A/Agilent (G005) at 20° C. (ε-parallel-cells with JALS 2096-R$^1$).

EXAMPLES

Synthesis Examples

Abbreviations:
dist. distilled
DABCO 1,4-Diazabicyclo[2.2.2]octane
THF Tetrahydrofuran
MTB ether Methyl-tert-butyl ether
XPhos 2-Dicyclohexylphosphino-2',4',6'-triisopropylbiphenyl
XPhos Pd G2 Chloro(2-dicyclohexylphosphino-2',4',6'-triisopropyl-1,1'-biphenyl)[2-(2'-amino-1,1'-biphenyl) palladium (II)

Synthesis Example 1: 4-Butyl-4'-[2-(3-Fluoro-4-Isothiocyanato-5-Methylphenyl)Ethynyl]-1,1'-biphenyl Step 1.1: [4-(4-Butylphenyl)Phenyl]Ethynyl-Trimethyl-Silane

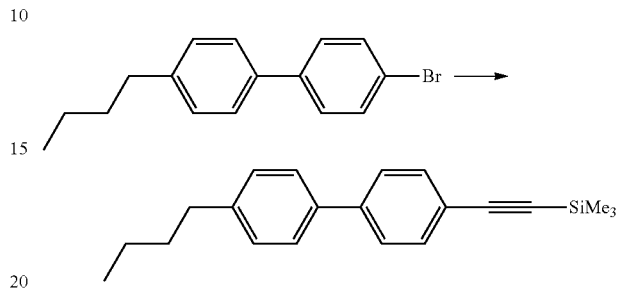

A mixture of 1-bromo-4-(4-butylphenyl)benzene (CAS 63619-54-5, 33.5 g, 116 mmol), triethylamine (135 mL), bis(triphenylphosphine)-palladium(II)-chloride (3.2 g, 4.6 mmol), copper(I)-iodide (530 mg, 2.8 mmol) and trimethylsilyl acetylene (33.6 mL, 237 mmol) is heated at reflux temperature overnight. Then dist. water and MTB-ether are added to the reaction mixture. The layers are separated, and the aqueous layer is extracted with MTB-ether. The combined organic layers are washed with dist. water, dried (sodium sulfate) and concentrated in vacuo. The residue is purified by flash chromatography (heptane) to give [4-(4-butylphenyl)phenyl]ethynyl-trimethyl-silane as an orange solid.

Step 1.2: 1-Butyl-4-(4-Ethynylphenyl)Benzene

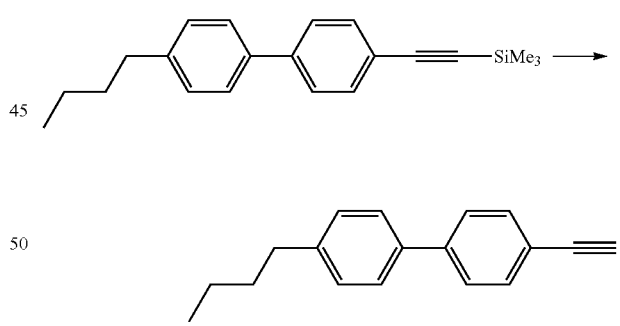

Tetra-n-butylammonium fluoride (113 mL, 1 M in THF) is added slowly to a solution of [4-(4-butylphenyl)phenyl] ethynyl-trimethyl-silane (34.6 g, 113 mmol) in THF (650 mL) at 10° C. The reaction mixture is stirred at room temperature overnight. Then dist. water, hydrochloric acid (1 M) and MTB-ether are added to the reaction mixture. The phases are separated, and the aqueous phase is extracted with MTB-ether. The combined organic phases are washed with brine, dried (sodium sulfate) and concentrated in vacuo. The residue is purified by flash chromatography (heptane) to give 1-butyl-4-(4-ethynylphenyl)benzene as a light yellow solid.

Step 1.3: 4-(2-{4'-Butyl-[1,1'-Biphenyl]-4-yl}Ethynyl)-2-Fluoro-6-Methylaniline

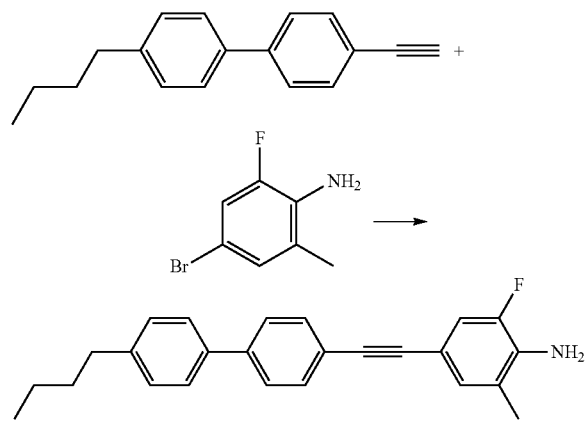

A mixture of 1-butyl-4-(4-ethynylphenyl)benzene (4.0 g, 17 mmol) and 4-bromo-2-fluoro-6-methylaniline (3.6 g, 17 mmol) in diisopropylamine (40 mL) and THF (40 mL) is heated to 70° C. under nitrogen atmosphere. Then XPhos PD G2 (27 mg, 0.03 mmol), XPhos (16 mg, 0.03 mmol) and copper(I)-iodide (3.3 mg, 0.02 mmol) are added, and the reaction mixture is stirred at 70° C. overnight. Then it is filtered and concentrated in vacuo. The residue is purified by flash chromatography (heptane and heptane/MTB-ether) to give 4-(2-{4'-butyl-[1,1'-biphenyl]-4-yl}ethynyl)-2-fluoro-6-methylaniline as a light brown solid.

Step 1.4: 4-Butyl-4'-[2-(3-Fluoro-4-Isothiocyanato-5-Methylphenyl)Ethynyl]-1,1'-Biphenyl

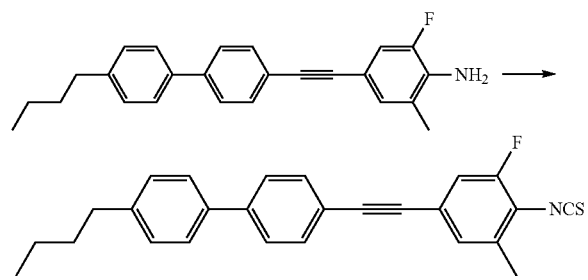

Thiophosgene (1.75 mL, 22 mmol) is added dropwise to a mixture of 4-(2-{4'-butyl-[1,1'-biphenyl]-4-yl}ethynyl)-2-fluoro-6-methylaniline (7.2 g, 20 mmol) and 1,4-diazabicyclo[2.2.2]octane (5.6 g, 50 mmol) in dichloromethane (75 mL) at 0° C., and the reaction mixture is stirred for 1 h at room temperature. It is hydrolyzed with brine, and the phases are separated. The aqueous phase is washed with dichloromethane, and the combined organic phases are dried (sodium sulfate) and concentrated in vacuo. The residue is purified by flash chromatography (heptane) and crystallization with heptane to give 4-butyl-4'-[2-(3-fluoro-4-isothiocyanato-5-methylphenyl)ethynyl]-1,1'-biphenyl as pale yellow crystals Phase sequence: K 83 SmA 102 N 172 I
$\Delta n = 0.4800$
$\Delta \varepsilon = 14.4$

Synthesis Example 2: 5-[2-(4-Butylphenyl)Ethynyl]-1-Fluoro-2-Isothiocyanato-3-Methylbenzene

Step 2.1: 4-[2-(4-Butylphenyl)Ethynyl]-2-Fluoro-6-Methylaniline

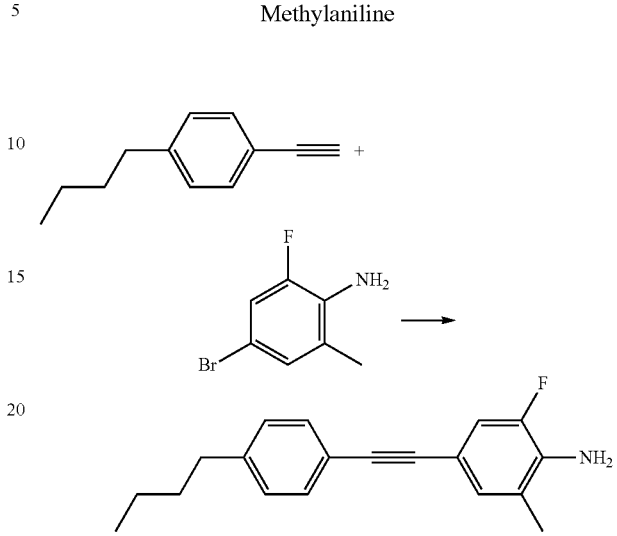

A solution of 1-butyl-4-ethynylbenzene (CAS 79887-09-5) (3.0 g, 19 mmol) and 4-bromo-2-fluoro-6-methylaniline (CAS 429683-46-5) (3.9 g, 19 mmol) in diisopropylamine (45 mL) and tetrahydrofuran (50 mL) is heated to 70° C. under nitrogen atmosphere. Then XPhos Pd G2 (30 mg, 0.04 mmol), XPhos (18 mg, 0.04 mmol) and copper(I)-iodide (3.6 mg, 0.02 mmol) are added, and the reaction mixture is stirred at 70° C. 72 h. Then it is filtered and concentrated in vacuo. The residue is purified by silica gel chromatography with heptane/toluene to give 4-[2-(4-butylphenyl)ethynyl]-2-fluoro-6-methylaniline as a light brown oil.

Step 2.2: 5-[2-(4-Butylphenyl)Ethynyl]-1-Fluoro-2-Isothiocyanato-3-Methylbenzene

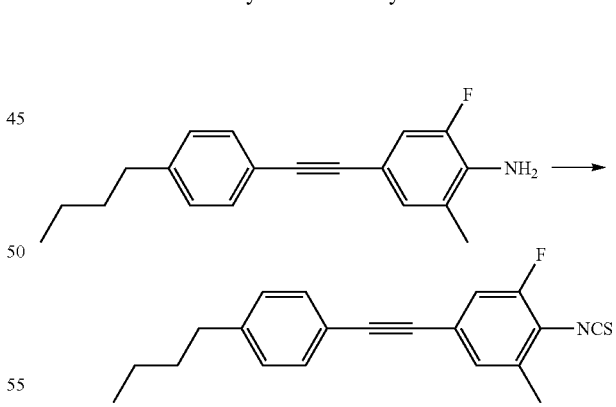

Thiophosgene (1.5 mL, 20 mmol) is added dropwise to a mixture of 4-[2-(4-butylphenyl)ethynyl]-2-fluoro-6-methylaniline (5.0 g, 18 mmol) and DABCO (5.0 g, 44 mmol) in dichloromethane (65 mL) at 0° C., and the reaction mixture is stirred for 1 h at room temperature. It is hydrolyzed with brine, and the phases are separated. The aqueous phase is washed with dichloromethane, and the combined organic phases are dried (sodium sulfate) and concentrated in vacuo. The residue is purified by silica gel chromatography with heptane and by RP flash chromatography with acetonitrile to give 5-[2-(4-butylphenyl)ethynyl]-1-fluoro-2-isothiocyanato-3-methylbenzene as a colorless oil.

Phase sequence: Tg-57 I
Δn=0.3367
Δε=13.2
γ₁=119 mPas

Synthesis Example 3: 4'-[2-(4-Butylphenyl)Ethynyl]-3-Fluoro-4-Isothiocyanato-5-Methyl-1,1'-Biphenyl Step 3.1: 2-Fluoro-6-Methyl-4-(4,4,5,5-Tetramethyl-1,3,2-Dioxaborolan-2-yl)Aniline

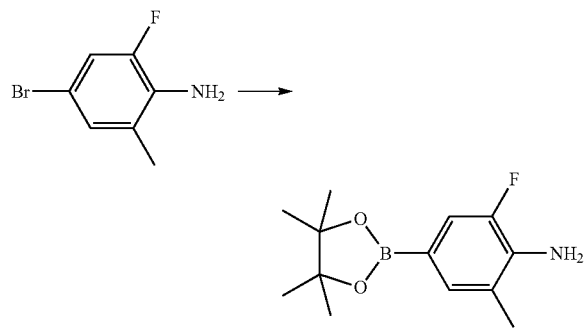

A mixture of 4-bromo-2-fluoro-6-methylaniline (CAS 429683-46-5, 17.0 g, 83 mmol), potassium acetate (24.5 g, 250 mmol), [1,1'-bis(diphenylphosphino)ferrocene]-dichloropalladium(II) (1.8 g, 2.5 mmol) and bis-(pinacolato)-diboron (25.9 g, 100 mmol) in 1,4-dioxane (200 mL) is heated at reflux temperature overnight. Then the reaction is quenched by addition of dist. water and MTB-ether. The phases are separated, and the aqueous phase is extracted with MTB-ether. The combined organic phases are washed with dist. water and brine, dried (sodium sulfate) and concentrated in vacuo.

The residue is purified by flash chromatography (dichloromethane) to give 2-fluoro-6-methyl-4-(4,4,5,5-tetramethyl-1,3,2-dioxaborolan-2-yl)aniline as an orange oil.

Step 3.2: 4'-Bromo-3-Fluoro-5-Methyl-[1,1'-Biphenyl]-4-Amine

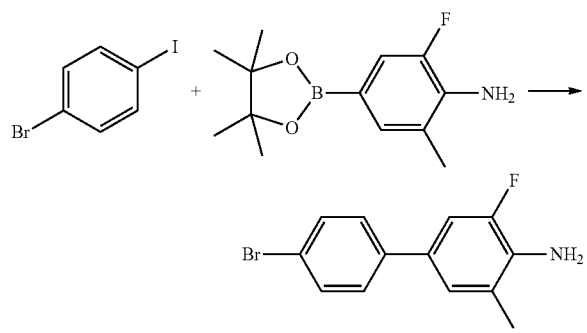

A mixture of 2-fluoro-6-methyl-4-(4,4,5,5-tetramethyl-1,3,2-dioxaborolan-2-yl)aniline (12.0 g, 48 mmol), 1-bromo-4-iodobenzene (15.2 g, 53 mmol) and sodium carbonate (12.2 g, 115 mmol) in isopropanol (30 mL), toluene (90 mL) and dist. water (65 mL) is stirred for 1 h under nitrogen atmosphere. Then bis(triphenylphosphino)-palladium(II)-dichloride (993 mg, 1.4 mmol) is added, and the reaction mixture is stirred at reflux temperature overnight. The phases are separated, and the aqueous phase is extracted with toluene. The combined organic phases are washed with dist. water, dried (sodium sulfate) and concentrated in vacuo. The residue is purified by flash chromatography (heptane/MTB-ether) to give 4'-bromo-3-fluoro-5-methyl-[1,1'-biphenyl]-4-amine as a colorless solid.

Step 3.3: 4'-[2-(4-Butylphenyl)Ethynyl]-3-Fluoro-5-Methyl-[1,1'-Biphenyl]-4-Amine

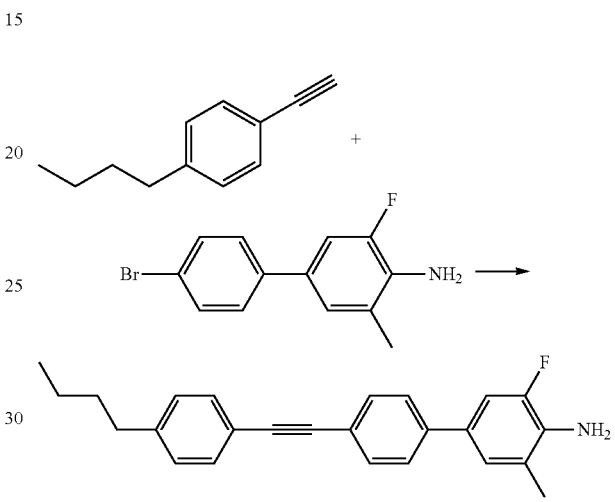

A mixture of 1-butyl-4-ethynylbenzene (CAS 79887-09-5, 1.5 g, 10 mmol) and 4'-bromo-3-fluoro-5-methyl-[1,1'-biphenyl]-4-amine (2.5 g, 9 mmol) in diisopropylamine (25 mL) and THF (25 mL) is slowly heated under nitrogen atmosphere. XPhos PD G2 (15 mg, 0.02 mmol), XPhos (9 mg, 0.02 mmol) and copper(I)-iodide (1.8 mg, 0.01 mmol) are added, the reaction mixture is stirred at reflux temperature for 4 h, is filtered and concentrated in vacuo. The residue is purified by flash chromatography (heptane and toluene) to give 4'-[2-(4-butylphenyl)ethynyl]-3-fluoro-5-methyl-[1,1'-biphenyl]-4-amine as a colorless solid.

Step 3.4: 4'-[2-(4-Butylphenyl)Ethynyl]-3-Fluoro-4-Isothiocyanato-5-Methyl-1,1'-Biphenyl Thiophosgene (0.6 mL, 8 mmol) is added dropwise to a mixture of 4'-[2-(4-butylphenyl)ethynyl]-3-fluoro-5-methyl-[1,1'-biphenyl]-4-amine (2.5 g, 7 mmol) and DABCO (2.0 g, 18 mmol) in dichloromethane (25 mL) at 0°

C. The reaction mixture is stirred for 1 h at room temperature, is hydrolyzed with brine, and the layers are separated. The aqueous phase is washed with dichloromethane, and the combined organic phases are dried (sodium sulfate) and concentrated in vacuo. The residue is purified by flash chromatography (heptane) and crystallization with heptane to give pale yellow crystals of 4'-[2-(4-butylphenyl)ethynyl]-3-fluoro-4-isothiocyanato-5-methyl-1,1'-biphenyl.

Phase sequence: K 73 SmA 172 I.
Δn=0.4652
Δε=16.5

Synthesis Example 4: 1-Fluoro-2-Isothiocyanato-3-Methyl-5-{2-[4-(4-Propylcyclohexyl)-Phenyl]Ethynyl}Benzene Step 4.1: 2-Fluoro-6-Methyl-4-{2-[4-(4-Propylcyclohexyl)Phenyl]Ethynyl}Aniline

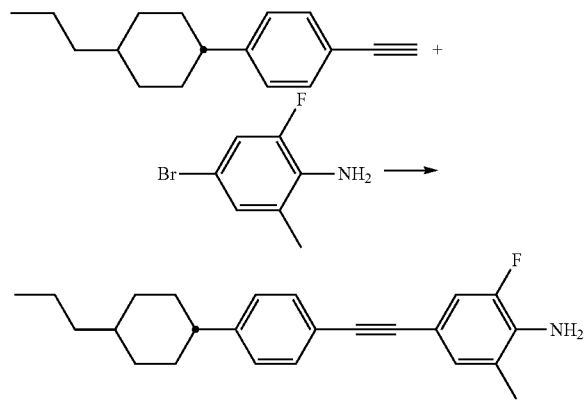

A solution of 4-(4-propyl-cyclohexyl)-phenylacetylene (CAS 167858-58-4) (5.4 g, 24 mmol) and 4-bromo-2-fluoro-6-methylaniline (CAS 429683-46-5) (4.6 g, 23 mmol) and diisopropylamine (55 mL) in THE (60 mL) is heated to 70° C. under nitrogen atmosphere. Then XPhos Pd G2 (35 mg, 0.05 mmol), XPhos (21 mg, 0.05 mmol) and copper(I)-iodide (4 mg, 0.02 mmol) are added, and the reaction mixture is stirred at 70° C. overnight. Then it is filtered and concentrated in vacuo. The residue is purified by silica gel chromatography (heptane/methyl tert-butyl ether) to give 2-fluoro-6-methyl-4-{2-[4-(4-propylcyclohexyl)phenyl]ethynyl}aniline as a light brown solid.

Step 4.2: 1-Fluoro-2-Isothiocyanato-3-Methyl-5-{2-[4-(4-Propylcyclohexyl)Phenyl]-Ethynyl}Benzene

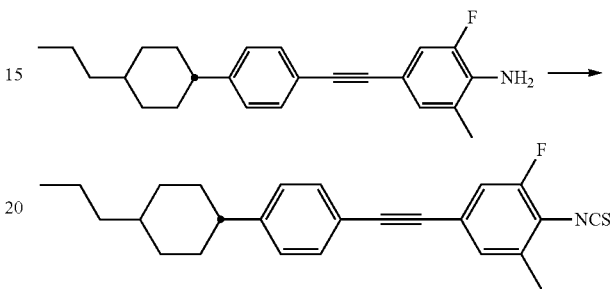

Thiophosgene (1.7 mL, 22 mmol) is added dropwise to a mixture of 2-fluoro-6-methyl-4-{2-[4-(4-propylcyclohexyl)phenyl]ethynyl}aniline (7.0 g, 20 mmol) and DABCO (5.6 g, 50 mmol) in dichloromethane (75 mL) at 0° C., and the reaction mixture is stirred for 1 h at room temperature. It is hydrolyzed with brine, and the phases are separated. The aqueous phase is washed with dichloromethane, and the combined organic phases are dried (sodium sulfate) and concentrated in vacuo. The residue is purified by silica gel chromatography (heptane) and crystallization with heptane. The crude product is purified by flash chromatography (toluene and heptane) and crystallization with heptane to give white crystals of 1-fluoro-2-isothiocyanato-3-methyl-5-{2-[4-(4-propylcyclohexyl)phenyl]ethynyl}benzene.

Phase sequence: K 89 N 109 I.
Δn=0.3722
Δε=13.9

In analogy to Synthesis Examples 1 to 4 the following compounds are obtained:

| No. | Compound | physical parameters |
|---|---|---|
| 5 | | |
| 6 | | |

| No. | Compound | physical parameters |
|-----|----------|---------------------|
| 7 | 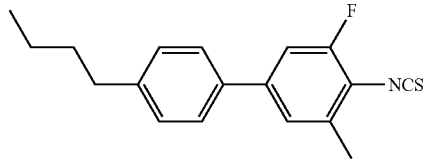 | |
| 8 | 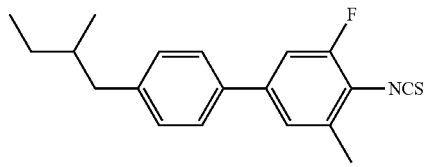 | |
| 9 | 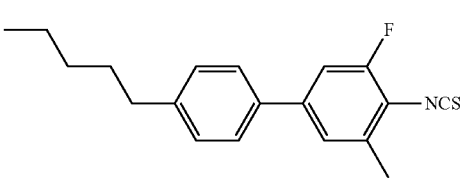 | |
| 10 | 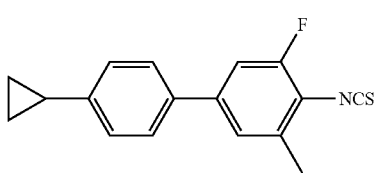 | |
| 11 | 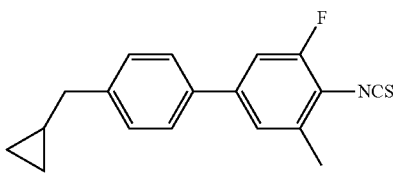 | |
| 12 | 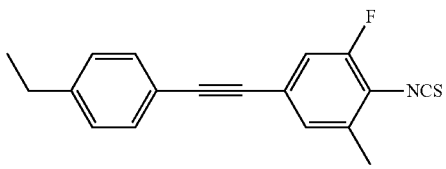 | |
| 13 | 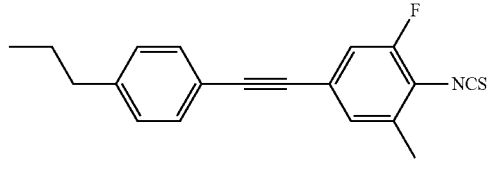 | |
| 14 | 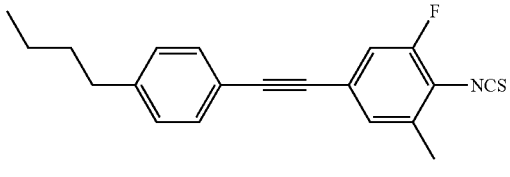 | |
| 15 | 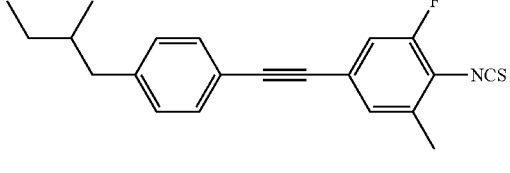 | |

-continued
| No. | Compound | physical parameters |
|---|---|---|
| 16 | 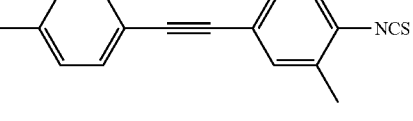 | |
| 17 | 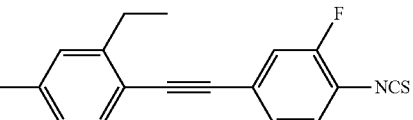 | |
| 18 |  | |
| 19 | 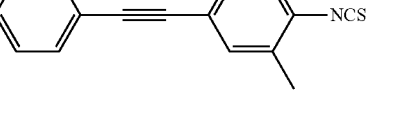 | |
| 20 | 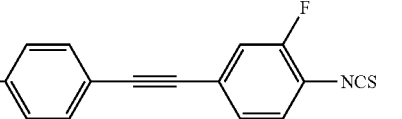 | |
| 21 | 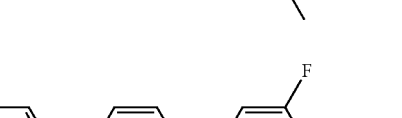 | |
| 22 | 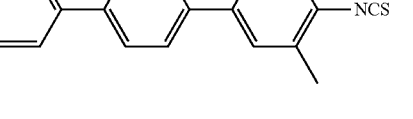 | |
| 23 | 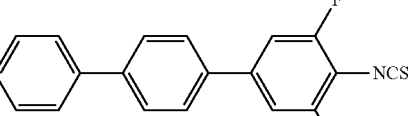 | |

-continued
| No. | Compound | physical parameters |
|---|---|---|
| 24 | 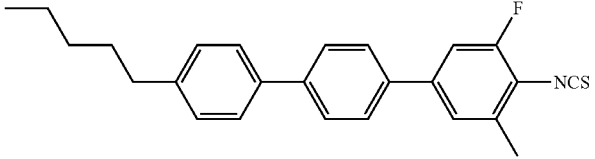 | |
| 25 | 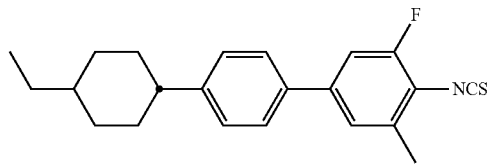 | |
| 26 | 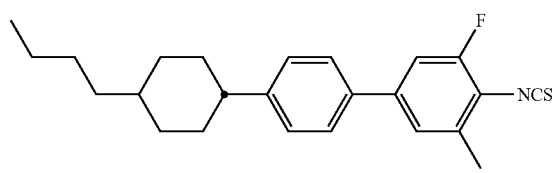 | |
| 27 | 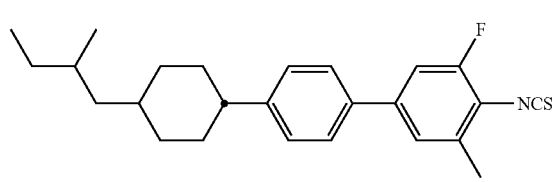 | |
| 28 | 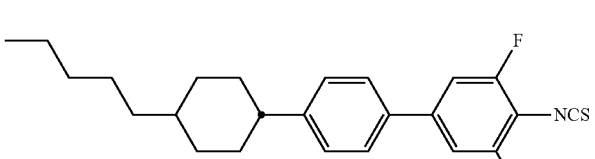 | |
| 29 | 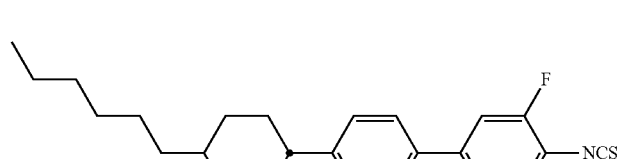 | |
| 30 |  | |
| 31 | 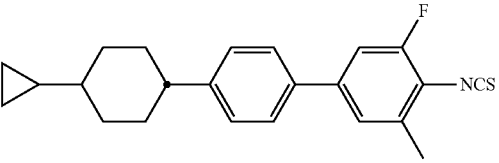 | |

-continued

| No. | Compound | physical parameters |
|-----|----------|---------------------|
| 32 | | |
| 33 | | |
| 34 | | |
| 35 | | |
| 36 | | |
| 37 | | |
| 38 | | |
| 39 | | |
| 40 | | |

| No. | Compound | physical parameters |
|---|---|---|
| 41 | 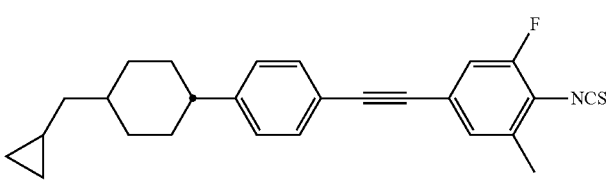 | |
| 42 | 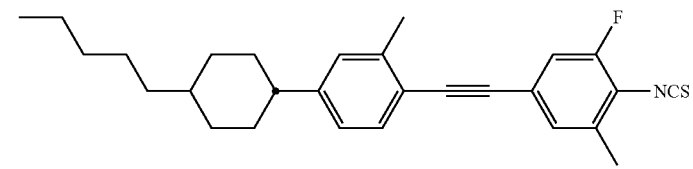 | |
| 43 | 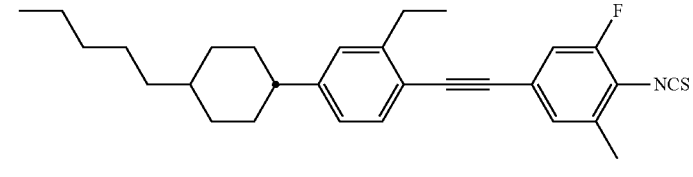 | |
| 44 | 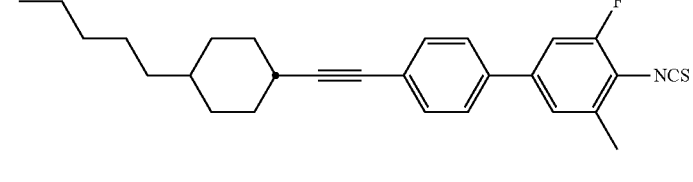 | |
| 45 | 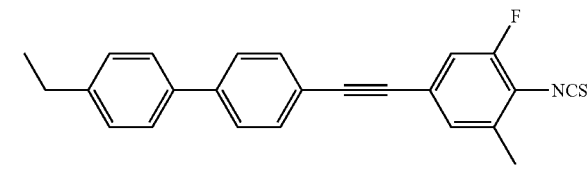 | |
| 46 | 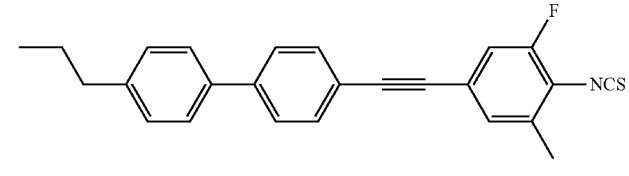 | |
| 47 | 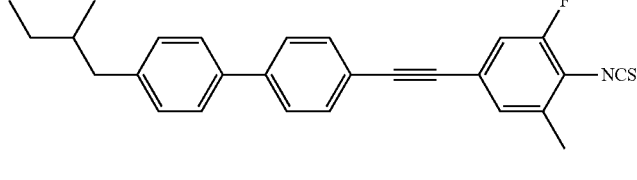 | |
| 48 | 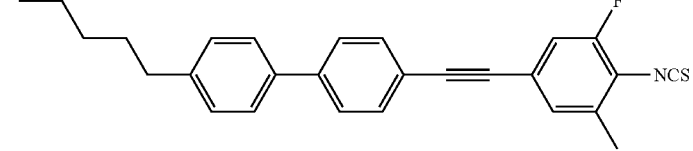 | |

-continued

| No. | Compound | physical parameters |
|---|---|---|
| 49 | | |
| 50 | | |
| 51 | | |
| 52 | | |
| 53 | | |
| 54 | | |
| 55 | | |
| 56 | | K 130 N 168 I<br>Δn = 0.4249<br>Δε = 1.5 |

-continued

| No. | Compound | physical parameters |
|---|---|---|
| 57 | F₃CO—⌬—⌬—C≡C—⌬(F)(CH₃)—NCS | K 99 N 168 I<br>Δn = 0.4070<br>Δε = 1.7 |
| 58 | Et—⌬—⌬(Cl)(CH₃)—NCS | |
| 59 | Pr—⌬—⌬(Cl)(CH₃)—NCS | |
| 60 | Bu—⌬—⌬(Cl)(CH₃)—NCS | |
| 61 | (2-methylbutyl)—⌬—⌬(Cl)(CH₃)—NCS | |
| 62 | Pentyl—⌬—⌬(Cl)(CH₃)—NCS | |
| 63 | cyclopropyl—⌬—⌬(Cl)(CH₃)—NCS | |
| 64 | cyclopropylmethyl—⌬—⌬(Cl)(CH₃)—NCS | |
| 65 | Et—⌬—C≡C—⌬(Cl)(CH₃)—NCS | |

-continued
| No. | Compound | physical parameters |
|---|---|---|
| 66 | 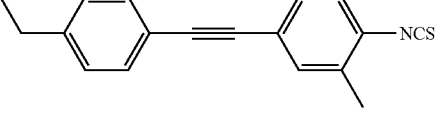 | |
| 67 |  | |
| 68 |  | |
| 69 | 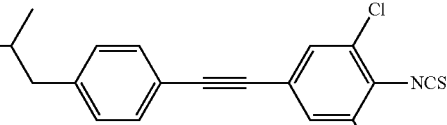 | |
| 70 |  | |
| 71 | 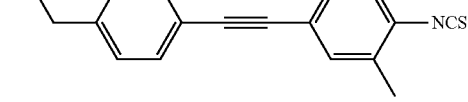 | |
| 72 | 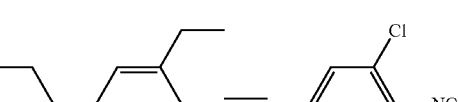 | |
| 73 |  | |

| No. | Compound | physical parameters |
|---|---|---|
| 74 | 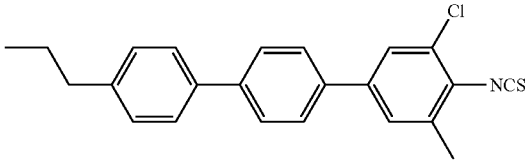 | |
| 75 | 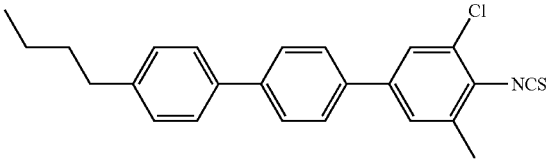 | |
| 76 | 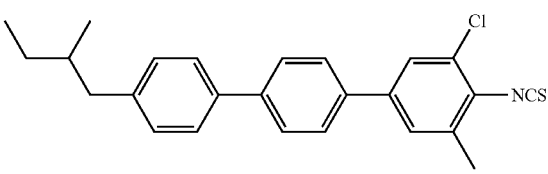 | |
| 77 | 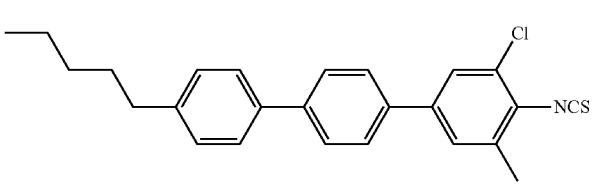 | |
| 78 | 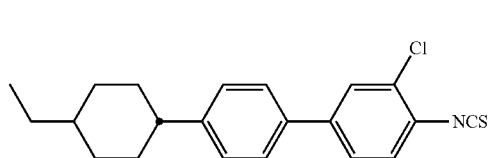 | |
| 79 | 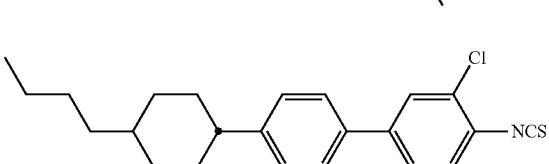 | |
| 80 | 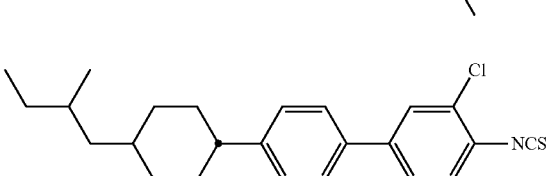 | |
| 81 | 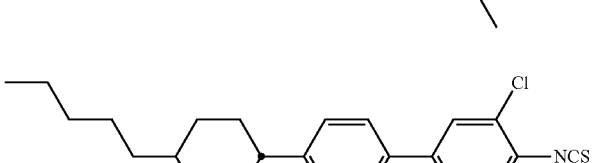 | |

-continued
| No. | Compound | physical parameters |
|---|---|---|
| 82 | 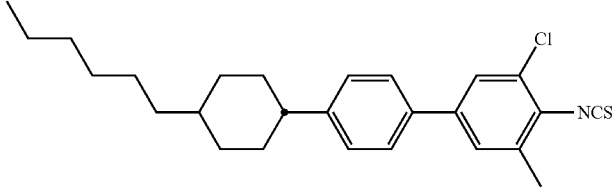 | |
| 83 | 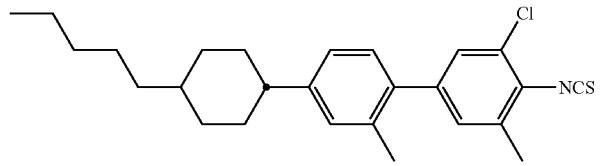 | |
| 84 | 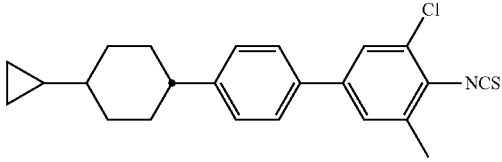 | |
| 85 | 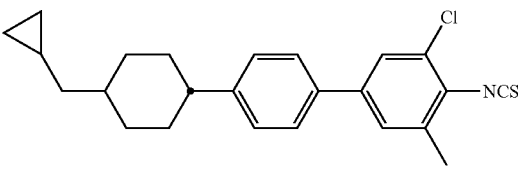 | |
| 86 | 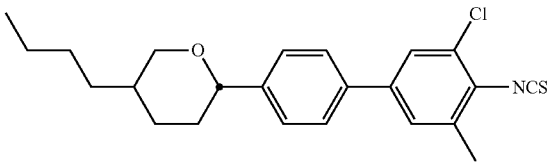 | |
| 87 | 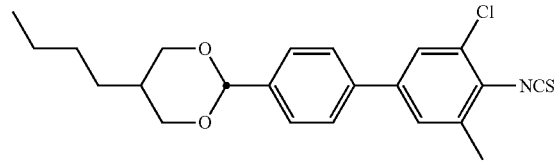 | |
| 88 | 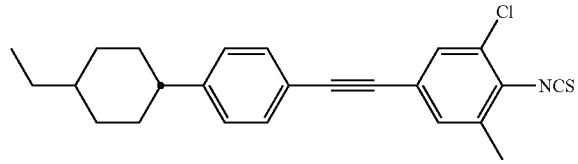 | |
| 89 | 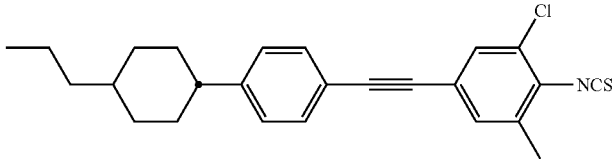 | |

| No. | Compound | physical parameters |
|-----|----------|---------------------|
| 90 | | |
| 91 | | |
| 92 | | |
| 93 | | |
| 94 | | |
| 95 | | |
| 96 | | |
| 97 | | |
| 98 | | |

| No. | Compound | physical parameters |
|---|---|---|
| 99 | propyl-C6H4-C6H4-C≡C-C6H2(Cl)(CH3)-NCS | |
| 100 | sec-butyl-C6H4-C6H4-C≡C-C6H2(Cl)(CH3)-NCS | |
| 101 | pentyl-C6H4-C6H4-C≡C-C6H2(Cl)(CH3)-NCS | |
| 102 | hexyl-C6H4-C6H4-C≡C-C6H2(Cl)(CH3)-NCS | |
| 103 | ethyl-C6H4-C≡C-C6H4-C6H2(Cl)(CH3)-NCS | |
| 104 | propyl-C6H4-C≡C-C6H4-C6H2(Cl)(CH3)-NCS | |
| 105 | butyl-C6H4-C≡C-C6H4-C6H2(Cl)(CH3)-NCS | |
| 106 | sec-butyl-C6H4-C≡C-C6H4-C6H2(Cl)(CH3)-NCS | |

| No. | Compound | physical parameters |
|---|---|---|
| 107 | 4-butyl-phenyl-C≡C-phenyl-(3-Cl,5-Me)phenyl-NCS | |
| 108 | 4-butyl-(2-Me)phenyl-C≡C-phenyl-(3-Cl,5-Me)phenyl-NCS | |
| 109 | F$_3$CO-phenyl-C≡C-phenyl-(3-Cl,5-Me)phenyl-NCS | |
| 110 | F$_3$CO-phenyl-phenyl-C≡C-(3-Cl,5-Me)phenyl-NCS | |

Application Test

The nematic liquid crystal host mixture N1, example mixtures M1 to M4 and comparative example mixtures C1 to C4 having the compositions and properties as indicated in the following tables are prepared and characterized with respect to their general physical properties and their applicability in microwave components at 19 GHz and 20° C.

The comparative mixtures contain compounds known from prior art corresponding to Synthesis Examples 1 to 4 in which the 1-fluoro-2-isothiocyanato-3-methyl-benzene head group is replaced with a 1,3-difluoro-2-isothiocyanato-benzene head group.

| Mixture N1 | | | |
|---|---|---|---|
| CPG-3-F | 12.0% | T(N, I) [° C.]: | 92.5 |
| CPG-5-F | 10.0% | Δn [589 nm, 20° C.]: | 0.0969 |
| CCEP-3-OT | 5.0% | $n_e$ [589 nm, 20° C.]: | 1.5764 |
| CCEP-5-OT | 5.0% | $n_o$ [589 nm, 20° C.]: | 1.4795 |
| CGPC-3-3 | 2.0% | Δε [1 kHz, 20° C.]: | 5.3 |
| CGPC-5-3 | 2.0% | $ε_∥$ [1 kHz, 20° C.]: | 8.4 |
| CGPC-5-5 | 2.0% | $ε_⊥$ [1 kHz, 20° C.]: | 3.1 |
| CP-6-F | 8.0% | $γ_1$ [mPa s, 20° C.]: | 128 |
| CP-7-F | 6.0% | $K_1$ [pN, 20° C.]: | 13.2 |
| CCP-2-OT | 8.0% | $K_3$ [pN, 20° C.]: | 19.6 |
| CCP-3-OT | 12.0% | $K_3/K_1$ [pN, 20° C.]: | 1.48 |
| CCP-4-OT | 7.0% | $V_0$ [V, 20° C.]: | 1.66 |
| CCP-5-OT | 11.0% | τ [20° C., 19 GHz]: | 0.100 |
| CP-5-F | 10.0% | $ε_{r,∥}$ [20° C., 19 GHz]: | 2.49 |
| Σ | 100.0% | $ε_{r,⊥}$ [20° C., 19 GHz]: | 2.24 |
| | | tan $δ_{ε\,r,∥}$ [20° C., 19 GHz]: | 0.0049 |
| | | tan $δ_{ε\,r,⊥}$ [20° C., 19 GHz]: | 0.0125 |
| | | η [20° C., 19 GHz]: | 8.0 |

Example Mixture M1 consists of 90% of host mixture N1 and 10% of the compound PPTG(1)-4-S of Synthesis Example 1.

Example Mixture M2 consists of 90% of host mixture N1 and 10% of the compound PTG(1)-4-S of Synthesis Example 2.

Example Mixture M3 consists of 90% of host mixture N1 and 10% of the compound PTPG(1)-4-S of Synthesis Example 3.

Example Mixture M4 consists of 90% of host mixture N1 and 10% of the compound CPTG(1)-3-S of Synthesis Example 4.

Comparative Mixture C1 consists of 90% of host mixture N1 and 10% of the compound PPTU-4-S.

Comparative Mixture C2 consists of 90% of host mixture N1 and 10% of the compound PTU-4-S.

Comparative Mixture C3 consists of 90% of host mixture N1 and 10% of the compound PTPU-4-S.
Comparative Mixture C4 consists of 90% of host mixture N1 and 10% of the compound CPTU-3-S.
The following results are obtained:

| Mixture: | $\varepsilon_{r,\|}$ | $\tan \delta_{\varepsilon\,r,\|}$ | $\varepsilon_{r,\perp}$ | $\tan \delta_{\varepsilon\,r,\perp}$ | $\tau$ | $\eta$ |
|---|---|---|---|---|---|---|
| M1 | 2.647 | 0.0045 | 2.305 | 0.0119 | 0.13 | 10.9 |
| C1 | 2.630 | 0.0047 | 2.293 | 0.0124 | 0.13 | 10.4 |
| M2 | 2.604 | 0.0052 | 2.272 | 0.0128 | 0.13 | 10.0 |
| C2 | 2.572 | 0.0055 | 2.249 | 0.0129 | 0.13 | 9.7 |
| M3 | 2.636 | 0.0048 | 2.278 | 0.0119 | 0.14 | 11.4 |
| C3 | 2.622 | 0.0046 | 2.286 | 0.0123 | 0.13 | 10.5 |
| M4 | 2.590 | 0.0045 | 2.264 | 0.0117 | 0.13 | 10.8 |
| C4 | 2.603 | 0.0050 | 2.278 | 0.0122 | 0.13 | 10.2 |

It can be seen that the compounds of formula G according to the invention show the same tunability values ($\tau$) as the compounds from the state of the art.

Surprisingly, the specific head group of the compounds according to the invention have improved miscibility with other polar compounds. As these polar compounds in general have limited solubility in a host material, it is possible to increase the overall proportion of compounds with high tunability in a medium and thus to achieve better tunabilities of media for microwave applications by addition of the compounds of formula G.

The invention claimed is:

1. A compound of formula G

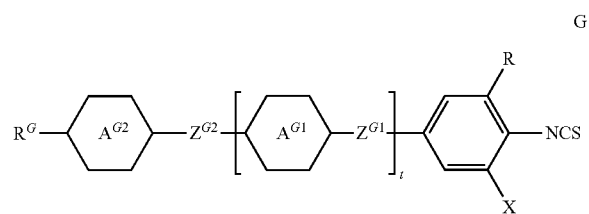

in which
R$^G$ denotes H, fluorinated or non-fluorinated straight chain having 1 to 12 C atoms, or fluorinated or non-fluorinated straight chain or branched alkenyl having 3 to 12 C atoms, in which one or more CH$_2$— groups may be replaced by

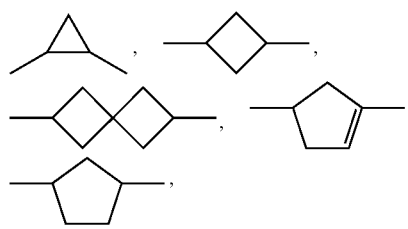

and in which one or more non-adjacent CH$_2$— groups may be replaced by —O—,
Z$^{G1}$ and Z$^{G2}$, identically or differently, denote —CH=CH—, —CF=CF—, —CH=CF—, —CF=CH—, —C≡C—, —C=C=C=C— or a single bond,
X denotes Cl or F,
R denotes linear or branched or cyclic alkyl having 3 to 6 C atoms,
t is 0, 1 or 2, and

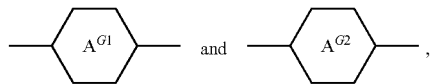

identically or differently, denote a radical selected from the following groups:

a) the group consisting of 1,4-phenylene, 1,4-naphthylene, and 2,6-naphthylene, in which one or two CH groups may be replaced by N and in which one or more H atoms may be replaced by L, b) the group consisting of trans-1,4-cyclohexylene, 1,4-cyclohexenylene, tetralin-2,6-diyl, tetralin-5,8-diyl, decalin-2,6-diyl, bicyclo [1.1.1] pentane -1,3-diyl, 4,4'-bicyclohexylene, bicyclo [2.2.2] octane-1,4-diyl, and spiro [3.3] -heptane-2,6-diyl, in which one or two CH groups may be replaced by N, one or more non-adjacent CH$_2$ groups may be replaced by —O— and/or —S— and in which one or more H atoms may be replaced by L, c) the group consisting of thiophene-2,5-diyl, thieno [3,2-b] thiophene-2,5-diyl, selenophene-2,5-diyl, each of which may also be mono- or polysubstituted by L, L on each occurrence, identically or differently, denotes F, Cl, CN, SCN, SF$_5$ or straight-chain or branched, in each case optionally fluorinated, alkyl, alkoxy, alkylcarbonyl, alkoxycarbonyl, alkylcarbonyloxy or alkoxycarbonyloxy each having 1 to 12 C atoms.

2. The compound according to claim 1, wherein R denotes methyl.

3. The compound according to claim 1, wherein X denotes fluorine.

4. The compound according to claim 1, wherein the compound is selected from the compounds of the formulae G-1 to G-6

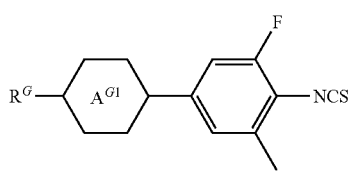

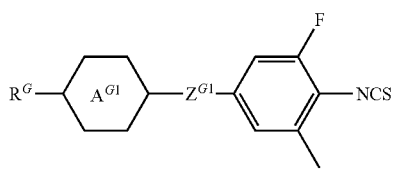

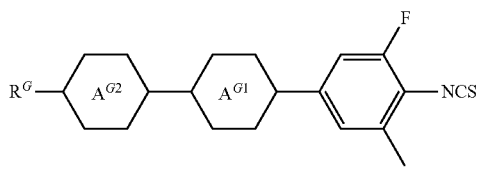

-continued
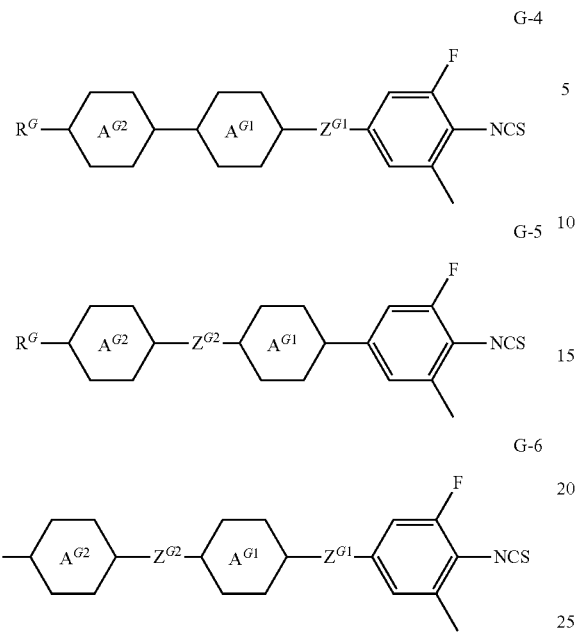
G-4
G-5
G-6
in which $R^G$, $Z^{G1}$, $Z^{G2}$,
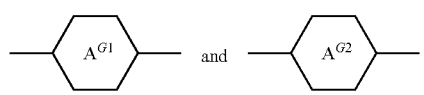
have the meanings given in claim 1.
5. The compound according to claim 1, wherein $Z^{G1}$ and $Z^{G2}$ denote —CF=CF— or —C≡C—.
6. The compound according to claim 1, wherein
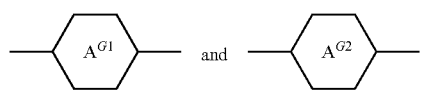
denote
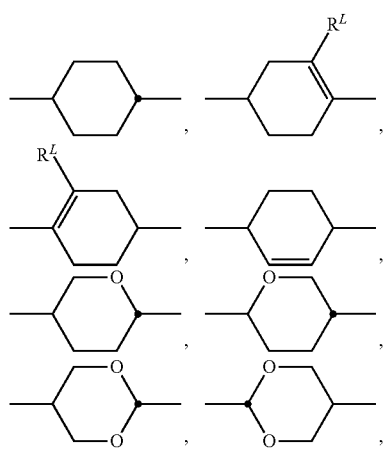
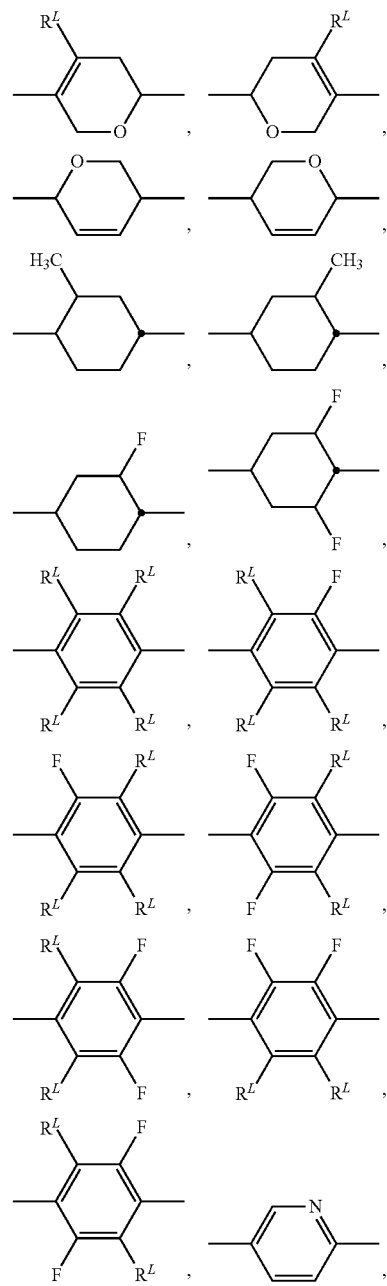
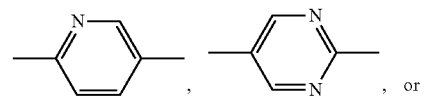
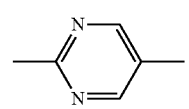

in which $R^L$, on each occurrence, identically or differently, denotes H or alkyl having 1 to 6 C atoms,
or denote

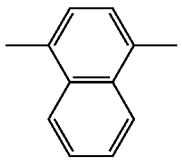 or 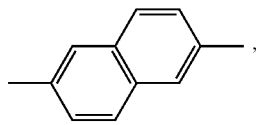, in which one or more H atoms may be replaced by a group $R^L$ or F, wherein $R^L$ denotes alkyl having 1 to 6 C atoms.

7. A liquid crystal medium comprising one or more compounds of formula G according to claim 1.

8. A component for high-frequency technology, comprising the liquid crystal medium according to claim 7.

9. The component according to claim 8, wherein the component is a liquid-crystal based antenna element, a phase shifter, a tunable filter, a tunable metamaterial structure, a matching network or a varactor.

10. A microwave antenna array, characterized in that it comprises one or more components according to claim 8.

11. A method for the production of a compound of formula G according to one or more of claims 1, characterized in that a compound of formula N

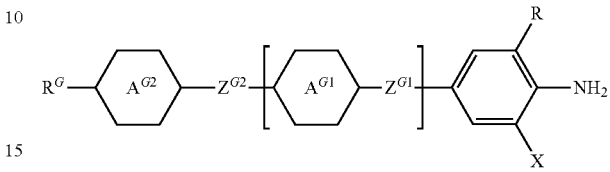

is reacted with carbon disulfide or with a thionocarbonic acid derivative X-C(=S)—Y, in which X and Y, identically or differently, denote a leaving group.

* * * * *